United States Patent
Edmondson et al.

(10) Patent No.: US 7,456,204 B2
(45) Date of Patent: Nov. 25, 2008

(54) CYCLOHEXYLGLYCINE DERIVATIVES AS DIPEPTIDYL PEPTIDASE INHIBITORS FOR THE TREATMENT OR PREVENTION OF DIABETES

(75) Inventors: Scott D. Edmondson, New York, NY (US); Anthony Mastracchio, Hoboken, NJ (US); Emma R. Parmee, Scotch Plains, NJ (US)

(73) Assignee: Merck & Co., Inc., Rahway, NJ (US)

( * ) Notice: Subject to any disclaimer, the term of this patent is extended or adjusted under 35 U.S.C. 154(b) by 562 days.

(21) Appl. No.: 10/560,771

(22) PCT Filed: Jun. 10, 2004

(86) PCT No.: PCT/US2004/018718

§ 371 (c)(1),
(2), (4) Date: Dec. 13, 2005

(87) PCT Pub. No.: WO2004/112701

PCT Pub. Date: Dec. 29, 2004

(65) Prior Publication Data

US 2007/0021477 A1    Jan. 25, 2007

Related U.S. Application Data

(60) Provisional application No. 60/479,246, filed on Jun. 17, 2003.

(51) Int. Cl.
  *A61K 31/428*  (2006.01)
  *A61K 31/423*  (2006.01)
  *A61K 31/4184* (2006.01)
  *C07D 277/60*  (2006.01)
  *C07D 263/52*  (2006.01)
  *C07D 235/02*  (2006.01)

(52) U.S. Cl. ............... 514/367; 548/152; 548/180; 548/217; 548/301.7; 548/302.7; 514/365; 514/374; 514/375; 514/385; 514/393

(58) Field of Classification Search ............ 548/146, 548/148, 152, 180, 215, 217, 300.1, 301.7, 548/302.7; 514/365, 367, 374, 375, 385, 514/393
See application file for complete search history.

(56) References Cited

U.S. PATENT DOCUMENTS

| | | | |
|---|---|---|---|
| 4,386,090 A | 5/1983 | Moinet et al. | |
| 5,939,560 A | 8/1999 | Jenkins et al. | |
| 6,011,155 A | 1/2000 | Villhauer | |
| 6,166,063 A | 12/2000 | Villhauer | |
| 6,303,661 B1 | 10/2001 | Demuth et al. | |
| 6,432,969 B1 | 8/2002 | Villhauer | |
| 6,699,871 B2 | 3/2004 | Edmondson et al. | |
| 7,098,239 B2 * | 8/2006 | Edmondson et al. | 514/423 |

FOREIGN PATENT DOCUMENTS

| | | |
|---|---|---|
| WO | WO 97/40832 | 11/1997 |
| WO | WO 98/19998 | 5/1998 |
| WO | WO 98/19998 A2 | 5/1998 |
| WO | WO 98/19998 A3 | 5/1998 |
| WO | WO 00/34241 | 6/2000 |
| WO | WO 01/34594 A1 | 5/2001 |
| WO | WO 01/42262 | 6/2001 |
| WO | WO 01/42262 A2 | 6/2001 |
| WO | WO 01/96295 A2 | 12/2001 |
| WO | WO 01/96295 A3 | 12/2001 |
| WO | WO 02/02560 A2 | 1/2002 |
| WO | WO 02/02560 A3 | 1/2002 |
| WO | WO 02/076450 A1 | 10/2002 |
| WO | WO 03/000180 A2 | 1/2003 |
| WO | WO 03/000180 A3 | 1/2003 |
| WO | WO 03/000181 A2 | 1/2003 |
| WO | WO 03/000181 A3 | 1/2003 |
| WO | WO 2005/002530 A2 | 1/2003 |
| WO | WO 03/082817 A2 | 10/2003 |
| WO | WO 2004/007468 | 1/2004 |
| WO | WO 2004/007468 A1 | 1/2004 |
| WO | WO 2004/032836 A2 | 4/2004 |
| WO | WO 2004/043940 | 5/2004 |
| WO | WO 2004/043940 A1 | 5/2004 |
| WO | WO 2004/050022 A2 | 6/2004 |

(Continued)

OTHER PUBLICATIONS

J. J. Holst, "Treatment of Type 2 Diabetes Mellitus with Agonists of the GLP-1 Receptor or DPP-IV Inhibitors", Expert Opin. Emerg. Drugs, vol. 9(1) pp. 155-166(2004).

(Continued)

*Primary Examiner*—Golam M Shameem
(74) *Attorney, Agent, or Firm*—Philippe L. Durette; Catherine D. Fitch

(57) ABSTRACT

The present invention is directed to novel cyclohexylglycine derivatives which are inhibitors of the dipeptidyl peptidase-IV enzyme ("DP-IV inhibitors") and which are useful in the treatment or prevention of diseases in which the dipeptidyl peptidase-IV enzyme is involved, such as diabetes and particularly type 2 diabetes. The invention is also directed to pharmaceutical compositions comprising these compounds and the use of these compounds and compositions in the prevention or treatment of such diseases in which the dipeptidyl peptidase-IV enzyme is involved.

22 Claims, No Drawings

FOREIGN PATENT DOCUMENTS

| | | |
|---|---|---|
| WO | WO 2004/058266 A1 | 7/2004 |
| WO | WO 2004/064778 A2 | 8/2004 |
| WO | WO 2004/069162 A2 | 8/2004 |
| WO | WO 2004/110436 | 12/2004 |
| WO | WO 2004/110436 A1 | 12/2004 |
| WO | WO 2004/112701 A2 | 12/2004 |
| WO | WO 2004/112701 A3 | 12/2004 |
| WO | WO 2005/011581 A2 | 2/2005 |
| WO | WO 2005/044195 A2 | 5/2005 |
| WO | WO 2005/056003 A1 | 6/2005 |
| WO | WO 2005/056013 A1 | 6/2005 |
| WO | WO 2005/108382 A1 | 11/2005 |
| WO | WO 2005-108382 A1 | 11/2005 |
| WO | WO2005/116029 A1 | 12/2005 |
| WO | WO 2005/116029 A1 | 12/2005 |
| WO | WO 2005/123685 A1 | 12/2005 |

OTHER PUBLICATIONS

C. F. Deacon, et al., "Inhibitors of dipeptidyl peptidase IV: A Novel Approach for the Prevention and Treatment of Type 2 Diabetes?", Expert Opin. Investig. Drugs, vol. 13(9) pp. 1091-1102( 2004).

K. Augustyns et al., "Dipeptidyl Peptidase IV Inhibitors as New Therapeutic Agents for the Treatment of Type 2 Diabetes", Expert Opin. Ther. Patents, vol. 13(4), pp. 499-510(2003).

Novartis AG: WO0034241, "Novel N-substituted-2-Cyanopyrrolidines as Potent Inhibitors of Dipeptidyl Peptidase IV in the Treatment of Non-Insulin-Dependent Diabetes Mellitus", Exp. Opin. Ther. Patents, vol. 10(12), pp. 1937-1942 (2000).

O. J. Orucker, "Therapeutic potential of dipeptidyl peptidase IV inhibitors for the treatment of type 2 diabetes", Exp. Opin Invest. Drugs, vol.12, pp. 87-100 (2004).

T. P. Vahl & D. A. D'Alessio, "Gut peptides in the treatment of diabetes mellitus" Exp. Opin. Invest. Drugs, vol. 13, pp. 177-188 (2004).

L. B. Knudsen, "Glucagon-like peptide-1: The Basis of a New Class of Treatment for Type 2 Diabetes", J. Med. Chem, vol. 47, pp. 4128-4134 (2004).

A. E. Weber, "Dipeptidyl Peptidase IV Inhibitors for the Treatment of Diabetes", J. Med. Chem, vol. 47, pp. 4135-4141 (2004).

J. J. Holst and C. F. Deacon, "Glucagon-like peptide 1 and inhibitors of dipeptidyl peptidase IV in the treatment of type 2 diabetes mellitus", Curr. Opin Pharmacology, vol. 4, pp. 589-596 (2004).

C. F. Deacon, "Perspectives in Diabetes—Therapeutic Strategies Based on Glucagon-Like Peptide 1", Diabetes, vol. 53, pp. 2181-2189 (2004).

K. Augustyns, et al., "Inhibitors of proline-specific dipeptidyl peptidase: DPP IV inhibitors as a novel approach for the treatment of Type 2 diabetes", Expert Opin. Ther. Patents, vol. 15(10), pp. 1387-1407 (2005).

Hans-Ulrich Demuth, et al., "Type 2 diabetes—Therapy with dipetidyl peptidase IV inhibitors", Biochimica et Biophysica Acta, vol. 1751, pp. 33-44 (2005).

Augustyns, K. et al., "Dipeptidyl peptidase IV inhibitors as new therapeutic agents for the treatment of Type 2 diabetes", Expert Opin. Ther. Patents, vol. 13, No. 4, pp. 499-510, 2003.

Augustyns, K. et al., "Inhibitors of proline-specific dipeptidyl peptidases: DPP IV inhibitors as a novel approach for the treatment of Type 2 diabetes", Expert Opin. Ther. Patent, vol. 15, No. 10, pp. 1387-1407, 2005.

Deacon, C. F., "*Perspectives in Diabetes*—Therapeutic Strategies Based on Glucagon-Like Peptide 1", Diabetes, vol. 53, pp. 2181-2189, 2004.

Deacon, C. F. et al., "Inhibitors of dipeptidyl peptidase IV: a novel approach for the prevention and treatment of Type 2 diabetes?", Expert Opin. Investig. Drugs, vol. 13, No. 9, pp. 1091-1102, 2004.

Demuth, H. U. et al., "Type 2 diabetes—Therapy with dipeptidyl peptidase IV inhibitors", Biochimica et Biophysica Acta, vol. 1751, pp. 33-44, 2005.

Drucker, D. J., "Therapeutic potential of dipeptidyl peptidase IV inhibitors for the treatment of type 2 diabetes", Expert Opin. Investig. Drugs, vol. 12, No. 1, pp. 87-100, 2003.

Holst, J. J., "Treatment of Type 2 diabetes mellitus with agonists of the GLP-1 receptor or DPP-IV inhibitors", Expert Opin. Emerg. Drugs, vol. 9, No. 1, pp. 155-166, 2004.

Holst, J. J. et al., "Glucagon-like peptide 1 and inhibitors of dipeptidyl peptidase IV in the treatment of type 2 diabetes mellitus", Current Opinion Pharmacology, vol. 4, pp. 589-596, 2004.

Knudsen, L. B., "Glucagon-like Peptide-1: The Basis of a New Class of Treatment for Type 2 Diabetes", J. Med. Chem, vol. 47, pp. 4128-4134, 2004.

Novartis AG: WO0034241—"Novel N-substituted-2-cyanopyrrolidines as potent inhibitors of dipeptidyl peptidase IV in the treatment of non-insulin-dependent diabetes mellitus", Exp. Opin. Ther. Patents, vol. 10, No. 12, pp. 1937-1942, 2000.

Vahl, T. P. et al., "Gut peptides in the treatment of diabetes mellitus", Expert Opin. Investig. Drugs, vol. 13, No. 3, pp. 177-188, 2004.

Weber, A. E., "Dipeptidyl Peptidase IV Inhibitors for the Treatment of Diabetes", J. Med. Chem., vol. 47, pp. 4135-4141, 2004.

* cited by examiner

US 7,456,204 B2

CYCLOHEXYLGLYCINE DERIVATIVES AS DIPEPTIDYL PEPTIDASE INHIBITORS FOR THE TREATMENT OR PREVENTION OF DIABETES

CROSS REFERENCE TO RELATED APPLICATIONS

This application is the National Stage of International Application No. PCT/US04/018718, filed 10 Jun. 2004, which claims the benefit under 35 U.S.C. 119(e) of U.S. Provisional Application No. 60/479,246, filed 17 Jun. 2003.

FIELD OF THE INVENTION

The present invention relates to novel cyclohexylglycine derivatives which are inhibitors of the dipeptidyl peptidase-IV enzyme ("DP-IV inhibitors") and which are useful in the treatment or prevention of diseases in which the dipeptidyl peptidase-IV enzyme is involved, such as diabetes and particularly type 2 diabetes. The invention is also directed to pharmaceutical compositions comprising these compounds and the use of these compounds and compositions in the prevention or treatment of such diseases in which the dipeptidyl peptidase-IV enzyme is involved.

BACKGROUND OF THE INVENTION

Diabetes refers to a disease process derived from multiple causative factors and characterized by elevated levels of plasma glucose, or hyperglycemia in the fasting state or after administration of glucose during an oral glucose tolerance test. Persistent or uncontrolled hyperglycemia is associated with increased and premature morbidity and mortality. Often abnormal glucose homeostasis is associated both directly and indirectly with alterations of the lipid, lipoprotein and apolipoprotein metabolism and other metabolic and hemodynamic disease. Therefore patients with Type 2 diabetes mellitus are at especially increased risk of macrovascular and microvascular complications, including coronary heart disease, stroke, peripheral vascular disease, hypertension, nephropathy, neuropathy, and retinopathy. Therefore, therapeutical control of glucose homeostasis, lipid metabolism and hypertension are critically important in the clinical management and treatment of diabetes mellitus.

There are two generally recognized forms of diabetes. In type 1 diabetes, or insulin-dependent diabetes mellitus (IDDM), patients produce little or no insulin, the hormone which regulates glucose utilization. In type 2 diabetes, or noninsulin dependent diabetes mellitus (NIDDM), patients often have plasma insulin levels that are the same or even elevated compared to nondiabetic subjects; however, these patients have developed a resistance to the insulin stimulating effect on glucose and lipid metabolism in the main insulin-sensitive tissues, which are muscle, liver and adipose tissues, and the plasma insulin levels, while elevated, are insufficient to overcome the pronounced insulin resistance.

Insulin resistance is not primarily due to a diminished number of insulin receptors but to a post-insulin receptor binding defect that is not yet understood. This resistance to insulin responsiveness results in insufficient insulin activation of glucose uptake, oxidation and storage in muscle and inadequate insulin repression of lipolysis in adipose tissue and of glucose production and secretion in the liver.

The available treatments for type 2 diabetes, which have not changed substantially in many years, have recognized limitations. While physical exercise and reductions in dietary intake of calories will dramatically improve the diabetic condition, compliance with this treatment is very poor because of well-entrenched sedentary lifestyles and excess food consumption, especially of foods containing high amounts of saturated fat. Increasing the plasma level of insulin by administration of sulfonylureas (e.g. tolbutamide and glipizide) or meglitinide, which stimulate the pancreatic β-cells to secrete more insulin, and/or by injection of insulin when sulfonylureas or meglitinide become ineffective, can result in insulin concentrations high enough to stimulate the very insulin-resistant tissues. However, dangerously low levels of plasma glucose can result from administration of insulin or insulin secretagogues (sulfonylureas or meglitinide), and an increased level of insulin resistance due to the even higher plasma insulin levels can occur. The biguanides increase insulin sensitivity resulting in some correction of hyperglycemia. However, the two biguanides, phenformin and metformin, can induce lactic acidosis and nausea/diarrhea. Metformin has fewer side effects than phenformin and is often prescribed for the treatment of Type 2 diabetes.

The glitazones (i.e. 5-benzylthiazolidine-2,4-diones) are a more recently described class of compounds with potential for ameliorating many symptoms of type 2 diabetes. These agents substantially increase insulin sensitivity in muscle, liver and adipose tissue in several animal models of type 2 diabetes resulting in partial or complete correction of the elevated plasma levels of glucose without occurrence of hypoglycemia. The glitazones that are currently marketed are agonists of the peroxisome proliferator activated receptor (PPAR), primarily the PPAR-gamma subtype. PPAR-gamma agonism is generally believed to be responsible for the improved insulin sensititization that is observed with the glitazones. Newer PPAR agonists that are being tested for treatment of Type II diabetes are agonists of the alpha, gamma or delta subtype, or a combination of these, and in many cases are chemically different from the glitazones (i.e., they are not thiazolidinediones). Serious side effects (e.g. liver toxicity) have occurred with some of the glitazones, such as troglitazone.

Additional methods of treating the disease are still under investigation. New biochemical approaches that have been recently introduced or are still under development include treatment with alpha-glucosidase inhibitors (e.g. acarbose) and protein tyrosine phosphatase-1B (PTP-1B) inhibitors.

Compounds that are inhibitors of the dipeptidyl peptidase-IV ("DP-IV" or "DPP-IV") enzyme are also under investigation as drugs that may be useful in the treatment of diabetes, and particularly type 2 diabetes. See for example WO 97/40832, WO 98/19998, U.S. Pat. No. 5,939,560, Bioorg. Med. Chem. Lett., 6: 1163-1166 (1996); and Bioorg. Med. Chem. Lett., 6: 2745-2748 (1996). The usefulness of DP-IV inhibitors in the treatment of type 2 diabetes is based on the fact that DP-IV in vivo readily inactivates glucagon like peptide-1 (GLP-1) and gastric inhibitory peptide (GIP). GLP-1 and GIP are incretins and are produced when food is consumed. The incretins stimulate production of insulin. Inhibition of DP-IV leads to decreased inactivation of the incretins, and this in turn results in increased effectiveness of the incretins in stimulating production of insulin by the pancreas. DP-IV inhibition therefore results in an increased level of serum insulin. Advantageously, since the incretins are produced by the body only when food is consumed, DP-IV inhibition is not expected to increase the level of insulin at inappropriate times, such as between meals, which can lead to excessively low blood sugar (hypoglycemia). Inhibition of DP-IV is therefore expected to increase insulin without increasing the risk of hypoglycemia, which is a dangerous side effect associated with the use of insulin secretagogues.

DP-IV inhibitors also have other therapeutic utilities, as discussed herein. DP-IV inhibitors have not been studied extensively to date, especially for utilities other than diabetes. New compounds are needed so that improved DP-IV inhibitors can be found for the treatment of diabetes and potentially other diseases and conditions. The therapeutic potential of DP-IV inhibitors for the treatment of type 2 diabetes is discussed by D. J. Drucker in *Exp. Opin. Invest. Drugs,* 12: 87-100 (2003) and by K. Augustyns, et al., in *Exp. Opin. Ther. Patents,* 13: 499-510 (2003).

SUMARY OF THE INVENTION

The present invention is directed to novel cyclohexylglycine derivatives which are inhibitors of the dipeptidyl peptidase-IV enzyme ("DP-IV inhibitors") and which are useful in the treatment or prevention of diseases in which the dipeptidyl peptidase-IV enzyme is involved, such as diabetes and particularly type 2 diabetes. The invention is also directed to pharmaceutical compositions comprising these compounds and the use of these compounds and compositions in the prevention or treatment of such diseases in which the dipeptidyl peptidase-IV enzyme is involved.

DETAILED DESCRIPTION OF THE INVENTION

The present invention relates to novel cyclohexylglycine derivatives useful as inhibitors of dipeptidyl peptidase-IV. Compounds of the present invention are described by structural formula I:

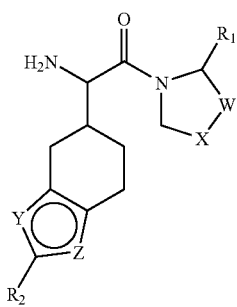

wherein:
each n is independently 0, 1, 2, or 3;
W is selected from the group consisting of $CH_2$, CHF, and $CF_2$;
X is selected from the group consisting of S, S(O), $S(O)_2$, $CH_2$, CHF, and $CF_2$;
Y and Z are each independently selected from the group consisting of O, S, N, and $NR^7$, with the proviso that at least one of Y and Z is N;
$R^1$ is hydrogen or cyano;
$R^2$ is selected from the group consisting of
hydrogen,
halogen,
cyano,
hydroxy,
$C_{1-6}$ alkyl, wherein alkyl is unsubstituted or substituted with one to five halogens,
$C_{1-6}$ alkoxy, wherein alkoxy is unsubstituted or substituted with one to five halogens, $(CH_2)_n$—COOH,
$(CH_2)_n$—$COOC_{1-6}$ alkyl,
$(CH_2)_n$—$CONR^3R^4$,
$(CH_2)_n$—$NR^3R^4$,
$(CH_2)_n$—$NR^6SO_2R^5$,
$(CH_2)_n$—$NR^6CONR^3R^4$,
$(CH_2)_n$—$NR^6COR^6$,
$(CH_2)_n$—$NR^6CO_2R^5$,
$(CH_2)_n$-aryl, wherein aryl is unsubstituted or substituted with one to five substituents independently selected from halogen, hydroxy, $CO_2H$,
$C_{1-6}$ alkyloxycarbonyl, $C_{1-6}$ alkyl, $C_{3-6}$ cycloalkyl, and $C_{1-6}$ alkoxy, wherein alkyl and alkoxy are unsubstituted or substituted with one to five halogens,
wherein any methylene ($CH_2$) carbon atom in $R^2$ is independently unsubstituted or substituted with one to two groups independently selected from halogen, hydroxy, and $C_{1-4}$ alkyl unsubstituted or substituted with one to five halogens;
$R^3$ and $R^4$ are independently selected from the group consisting of
hydrogen,
$(CH_2)_n$-phenyl,
$(CH_2)_n$—$C_{3-6}$ cycloalkyl, and
$C_{1-6}$ alkyl,
wherein alkyl is unsubstituted or substituted with one to five halogens and wherein phenyl and cycloalkyl are unsubstituted or substituted with one to five substituents independently selected from halogen, hydroxy, $C_{1-6}$ alkyl, and $C_{1-6}$ alkoxy, wherein alkyl and alkoxy are unsubstituted or substituted with one to five halogens; or
$R^3$ and $R^4$ together with the nitrogen atom to which they are attached form a heterocyclic ring selected from azetidine, pyrrolidine, piperidine, piperazine, and morpholine wherein said heterocyclic ring is unsubstituted or substituted with one to three substituents independently selected from halogen, hydroxy, $C_{1-6}$ alkyl, and
$C_{1-6}$ alkoxy, wherein alkyl and alkoxy are unsubstituted or substituted with one to five halogens;
each $R^5$ is independently selected from the group consisting of $(CH_2)_n$-phenyl, $(CH_2)_n$—$C_{3-6}$ cycloalkyl, and $C_{1-6}$ alkyl, wherein alkyl is unsubstituted or substituted with one to five halogens and wherein phenyl and cycloalkyl are unsubstituted or substituted with one to five substituents independently selected from halogen, hydroxy, $C_{1-6}$ alkyl, and $C_{1-6}$ alkoxy, wherein alkyl and alkoxy are unsubstituted or substituted with one to five halogens, and wherein any methylene ($CH_2$) carbon atom in $R^5$ is unsubstituted or substituted with one to two groups independently selected from halogen, hydroxy, and $C_{1-4}$ alkyl unsubstituted or substituted with one to five halogens;
each $R^6$ is hydrogen or $R^5$; and
$R^7$ is selected from the group consisting of
hydrogen,
$(CH_2)_n$-phenyl,
$(CH_2)_n$—$C_{3-6}$ cycloalkyl, and
$C_{1-6}$ alkyl,
wherein alkyl is unsubstituted or substituted with one to five halogens and wherein phenyl and cycloalkyl are unsubstituted or substituted with one to five substituents independently selected from halogen, hydroxy, $C_{1-6}$ alkyl, and $C_{1-6}$ alkoxy, wherein alkyl and alkoxy are unsubstituted or substituted with one to five halogens.

In one embodiment of the compounds of the present invention, the carbon atom marked with an * has the configuration as depicted in formula IIa:

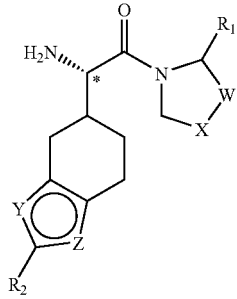

(IIa)

wherein W, X, Y, Z, R¹, and R² are as defined hereinabove.

In a second embodiment of the compounds of the present invention, W is CH₂, Y is S and Z is N as depicted in formula IIb:

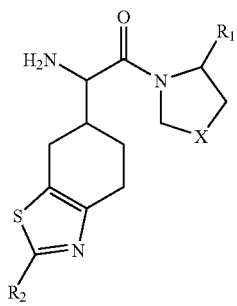

(IIb)

wherein X, R¹ and R² are as defined hereinabove.

In a class of this embodiment, X is CH₂, CHF, or CF₂. In a subclass of this class, R¹ is hydrogen. In another class of this embodiment, the carbon atom marked with an * has the configuration as depicted in formula IIc:

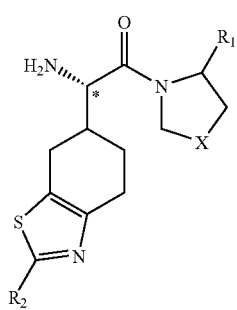

(IIc)

In a subclass of this class, X is CH₂, CHF, or CF₂ and R¹ is hydrogen.

In a third embodiment of the compounds of the present invention, W is CH₂, Y is N and Z is S as depicted in formula IId:

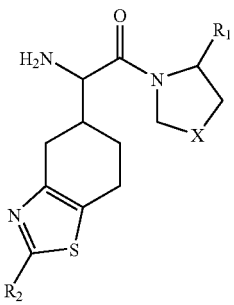

(IId)

wherein X, R¹ and R² are as defined hereinabove.

In a class of this embodiment, X is CH₂, CHF, or CF₂. In a subclass of this class, R¹ is hydrogen. In another class of this embodiment, the carbon atom marked with an * has the configuration as depicted in formula IIe:

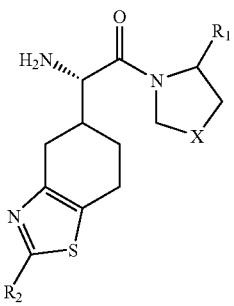

(IIe)

In a subclass of this class, X is CH₂, CHF, or CF₂ and R¹ is hydrogen.

In a fourth embodiment of the compounds of the present invention, W is CH₂, Y is O and Z is N as depicted in formula IIf:

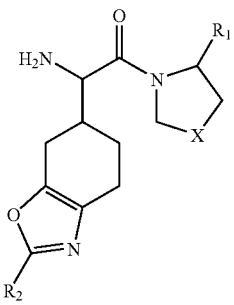

(IIf)

wherein X, R¹ and R² are as defined hereinabove.

In a class of this embodiment, X is CH₂, CHF, or CF₂. In a subclass of this class, R¹ is hydrogen. In another class of this embodiment, the carbon atom marked with an * has the configuration as depicted in formula IIg:

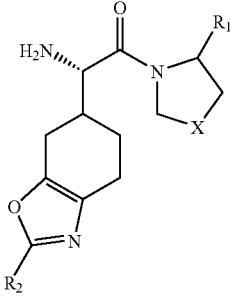

(IIg)

In a subclass of this class, X is CH$_2$, CHF, or CF$_2$ and R$^1$ is hydrogen.

In a fifth embodiment of the compounds of the present invention, W is CH$_2$, Y is N and Z is O as depicted in formula IIh:

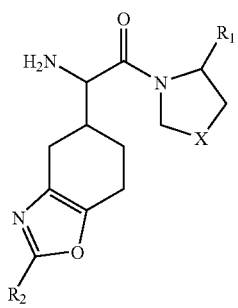

(IIh)

wherein X, R$^1$ and R$^2$ are as defined hereinabove.

In a class of this embodiment, X is CH$_2$, CHF, or CF$_2$. In a subclass of this class, R$^1$ is hydrogen. In another class of this embodiment, the carbon atom marked with an * has the configuration as depicted in formula IIi:

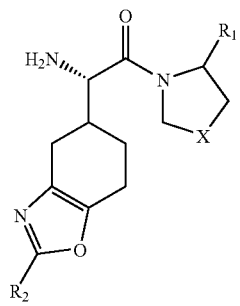

(IIi)

In a subclass of this class, X is CH$_2$, CHF, or CF$_2$ and R$^1$ is hydrogen.

In a sixth embodiment of the compounds of the present invention, W is CH$_2$, Y is N and Z is NR$^7$ as depicted in formula IIj:

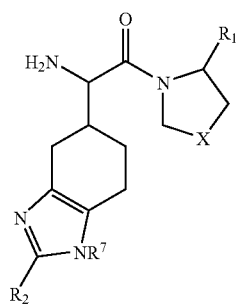

(IIj)

wherein X, R$^1$, R$^2$ and R$^7$ are as defined hereinabove.

In a class of this embodiment, X is CH$_2$, CHF, or CF$_2$. In a subclass of this class, R$^1$ is hydrogen. In another class of this embodiment, the carbon atom marked with an * has the configuration as depicted in formula IIk:

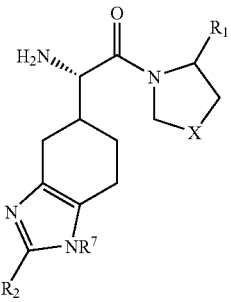

(IIk)

In a subclass of this class, X is CH$_2$, CHF, or CF$_2$ and R$^1$ is hydrogen.

In a seventh embodiment of the compounds of the present invention, W is CH$_2$, Y is NR$^7$ and Z is N as depicted in formula IIl:

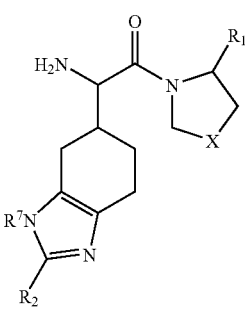

(IIl)

wherein X, R$^1$, R$^2$ and R$^7$ are as defined hereinabove.

In a class of this embodiment, X is CH$_2$, CHF, or CF$_2$. In a subclass of this class, R$^1$ is hydrogen. In another class of this embodiment, the carbon atom marked with an * has the configuration as depicted in formula IIm:

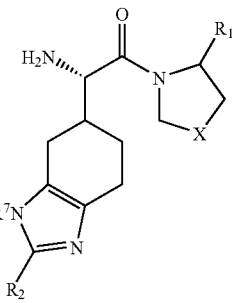

(IIm)

In a subclass of this class, X is CH$_2$, CHF, or CF$_2$ and R$^1$ is hydrogen.

As used herein the following definitions are applicable.

"Alkyl", as well as other groups having the prefix "alk", such as alkoxy and alkanoyl, means carbon chains which may be linear or branched, and combinations thereof, unless the carbon chain is defined otherwise. Examples of alkyl groups include methyl, ethyl, propyl, isopropyl, butyl, sec- and tert-butyl, pentyl, hexyl, heptyl, octyl, nonyl, and the like. Where the specified number of carbon atoms permits, e.g., from $C_{3-10}$, the term alkyl also includes cycloalkyl groups, and combinations of linear or branched alkyl chains combined with cycloalkyl structures. When no number of carbon atoms is specified, $C_{1-6}$ is intended.

"Cycloalkyl" is a subset of alkyl and means a saturated carbocyclic ring having a specified number of carbon atoms. Examples of cycloalkyl include cyclopropyl, cyclobutyl, cyclopentyl, cyclohexyl, cycloheptyl, cyclooctyl, and the like. A cycloalkyl group generally is monocyclic unless stated otherwise. Cycloalkyl groups are saturated unless otherwise defined.

The term "alkoxy" refers to straight or branched chain alkoxides of the number of carbon atoms specified (e.g., $C_{1-10}$ alkoxy), or any number within this range [i.e., methoxy (MeO—), ethoxy, isopropoxy, etc.].

The term "alkylthio" refers to straight or branched chain alkylsulfides of the number of carbon atoms specified (e.g., $C_{1-10}$ alkylthio), or any number within this range [i.e., methylthio (MeS—), ethylthio, isopropylthio, etc.].

The term "alkylamino" refers to straight or branched alkylamines of the number of carbon atoms specified (e.g., $C_{1-6}$ alkylamino), or any number within this range [i.e., methylamino, ethylamino, isopropylamino, t-butylamino, etc.].

The term "alkylsulfonyl" refers to straight or branched chain alkylsulfones of the number of carbon atoms specified (e.g., $C_{1-6}$ alkylsulfonyl), or any number within this range [i.e., methylsulfonyl (MeSO$_2$—), ethylsulfonyl, isopropylsulfonyl, etc.].

The term "alkyloxycarbonyl" refers to straight or branched chain esters of a carboxylic acid derivative of the present invention of the number of carbon atoms specified (e.g., $C_{1-6}$ alkyloxycarbonyl), or any number within this range [i.e., methyloxycarbonyl (MeOCO—), ethyloxycarbonyl, or butyloxycarbonyl].

"Aryl" means a mono- or polycyclic aromatic ring system containing carbon ring atoms. The preferred aryls are monocyclic or bicyclic 6-10 membered aromatic ring systems. Phenyl and naphthyl are preferred aryls. The most preferred aryl is phenyl.

"Heterocycle" and "heterocyclyl" refer to saturated or unsaturated non-aromatic rings or ring systems containing at least one heteroatom selected from O, S and N, further including the oxidized forms of suflir, namely SO and SO$_2$. Examples of heterocycles include tetrahydrofuran (THF), dihydrofuran, 1,4-dioxane, morpholine, 1,4-dithiane, piperazine, piperidine, 1,3-dioxolane, imidazolidine, imidazoline, pyrroline, pyrrolidine, tetrahydropyran, dihydropyran, oxathiolane, dithiolane, 1,3-dioxane, 1,3-dithiane, oxathiane, thiomorpholine, and the like.

"Heteroaryl" means an aromatic or partially aromatic heterocycle that contains at least one ring heteroatom selected from O, S and N. Heteroaryls also include heteroaryls fused to other kinds of rings, such as aryls, cycloalkyls and heterocycles that are not aromatic. Examples of heteroaryl groups include pyrrolyl, isoxazolyl, isothiazolyl, pyrazolyl, pyridinyl, 2-oxo-(1H)-pyridinyl (2-hydroxy-pyridinyl), oxazolyl, 1,2,4-oxadiazolyl, 1,3,4-oxadiazolyl, thiadiazolyl, thiazolyl, imidazolyl, triazolyl, tetrazolyl, furyl, triazinyl, thienyl, pyrimidinyl, pyrazinyl, benzisoxazolyl, benzoxazolyl, benzothiazolyl, benzothiadiazolyl, dihydrobenzofuranyl, indolinyl, pyridazinyl, indazolyl, isoindolyl, dihydrobenzothienyl, indolizinyl, cinnolinyl, phthalazinyl, quinazolinyl, naphthyridinyl, carbazolyl, benzodioxolyl, quinoxalinyl, purinyl, furazanyl, isobenzylfuranyl, benzimidazolyl, benzofuranyl, benzothienyl, quinolyl, indolyl, isoquinolyl, dibenzofuranyl, imidazo[1,2-α]pyridinyl, [1,2,4-triazolo][4,3-α]pyridinyl, pyrazolo[1,5-α]pyridinyl, [1,2,4-triazolo][1,5-α]pyridinyl, 2-oxo-1,3-benzoxazolyl, 4-oxo-3H-quinazolinyl, 3-oxo-[1, 2,4]-triazolo[4,3-α]-2H-pyridinyl, 5-oxo-[1,2,4]-4H-oxadiazolyl, 2-oxo-[1,3,4]-3H-oxadiazolyl, 2-oxo-1,3-dihydro-2H-imidazolyl, 3-oxo-2,4-dihydro-3H-1,2,4-triazolyl, and the like. For heterocyclyl and heteroaryl groups, rings and ring systems containing from 3-15 atoms are included, forming 1-3 rings.

"Halogen" refers to fluorine, chlorine, bromine and iodine. Chlorine and fluorine are generally preferred. Fluorine is most preferred when the halogens are substituted on an alkyl or alkoxy group (e.g. $CF_3O$ and $CF_3CH_2O$).

The compounds of the present invention may contain one or more asymmetric centers and can thus occur as racemates and racemic mixtures, single enantiomers, diastereomeric mixtures and individual diastereomers. The compounds of the present invention have one asymmetric center at the carbon atom marked with an * in formula Ia. Additional asymmetric centers may be present depending upon the nature of the various substituents on the molecule. Each such asymmetric center will independently produce two optical isomers and it is intended that all of the possible optical isomers and diastereomers in mixtures and as pure or partially purified compounds are included within the ambit of this invention. The present invention is meant to comprehend all such isomeric forms of these compounds.

Some of the compounds described herein contain olefinic double bonds, and unless specified otherwise, are meant to include both E and Z geometric isomers.

Some of the compounds described herein may exist as tautomers, which have different points of attachment of hydrogen accompanied by one or more double bond shifts. For example, a ketone and its enol form are keto-enol tautomers. The individual tautomers as well as mixtures thereof are encompassed with compounds of the present invention.

Formula I shows the structure of the class of compounds without preferred stereochemistry. Formula Ia shows the preferred sterochemistry at the carbon atom to which is attached the amino group of the alpha-amino acid from which these compounds are prepared.

The independent syntheses of these diastereomers or their chromatographic separations may be achieved as known in the art by appropriate modification of the methodology disclosed herein. Their absolute stereochemistry may be determined by the x-ray crystallography of crystalline products or crystalline intermediates which are derivatized, if necessary, with a reagent containing an asymmetric center of known absolute configuration.

If desired, racemic mixtures of the compounds may be separated so that the individual enantiomers are isolated. The separation can be carried out by methods well known in the art, such as the coupling of a racemic mixture of compounds to an enantiomerically pure compound to form a diastereomeric mixture, followed by separation of the individual diastereomers by standard methods, such as fractional crystallization or chromatography. The coupling reaction is often the formation of salts using an enantiomerically pure acid or base. The diasteromeric derivatives may then be converted to the pure enantiomers by cleavage of the added chiral residue. The racemic mixture of the compounds can also be separated directly by chromatographic methods utilizing chiral stationary phases, which methods are well known in the art.

Alternatively, any enantiomer of a compound may be obtained by stereoselective synthesis using optically pure starting materials or reagents of known configuration by methods well known in the art.

It will be understood that, as used herein, references to the compounds of structural formula I are meant to also include the pharmaceutically acceptable salts, and also salts that are not pharmaceutically acceptable when they are used as precursors to the free compounds or their pharmaceutically acceptable salts or in other synthetic manipulations.

The compounds of the present invention may be administered in the form of a pharmaceutically acceptable salt. The term "pharmaceutically acceptable salt" refers to salts prepared from pharmaceutically acceptable non-toxic bases or acids including inorganic or organic bases and inorganic or organic acids. Salts of basic compounds encompassed within the term "pharmaceutically acceptable salt" refer to non-toxic salts of the compounds of this invention which are generally prepared by reacting the free base with a suitable organic or inorganic acid. Representative salts of basic compounds of the present invention include, but are not limited to, the following: acetate, benzenesulfonate, benzoate, bicarbonate, bisulfate, bitartrate, borate, bromide, camsylate, carbonate, chloride, clavulanate, citrate, dihydrochloride, edetate, edisylate, estolate, esylate, flimarate, gluceptate, gluconate, glutamate, glycollylarsanilate, hexylresorcinate, hydrabamine, hydrobromide, hydrochloride, hydroxynaphthoate, iodide, isothionate, lactate, lactobionate, laurate, malate, maleate, mandelate, mesylate, methylbromide, methylnitrate, methylsulfate, mucate, napsylate, nitrate, N-methylglucamine ammonium salt, oleate, oxalate, pamoate (embonate), palmitate, pantothenate, phosphate/diphosphate, polygalacturonate, salicylate, stearate, sulfate, subacetate, succinate, tannate, tartrate, teoclate, tosylate, triethiodide and valerate. Furthermore, where the compounds of the invention carry an acidic moiety, suitable pharmaceutically acceptable salts thereof-include, but are not limited to, salts derived from inorganic bases including aluminum, arnmonium, calcium, copper, ferric, ferrous, lithium, magnesium, manganic, mangamous, potassium, sodium, zinc, and the like. Particularly preferred are the ammonium, calcium, magnesium, potassium, and sodium salts. Salts derived from pharmaceutically acceptable organic non-toxic bases include salts of primary, secondary, and tertiary amines, cyclic amines, and basic ion-exchange resins, such as arginine, betaine, caffeine, choline, N,N-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromnine, triethylamine, trimethylamine, tripropylamine, tromethamine, and the like.

Also, in the case of a carboxylic acid (—COOH) or alcohol group being present in the compounds of the present invention, pharmaceutically acceptable esters of carboxylic acid derivatives, such as methyl, ethyl, or pivaloyloxymethyl, or acyl derivatives of alcohols, such as acetate or maleate, can be employed. Included are those esters and acyl groups known in the art for modifying the solubility or hydrolysis characteristics for use as sustained-release or prodrug formulations.

Solvates, and in particular, the hydrates of the compounds of structural formula I are included in the present invention as well.

Exemplifying the invention is the use of the compounds disclosed in the Examples and herein.

The subject compounds are useful in a method of inhibiting the dipeptidyl peptidase-IV enzyme in a patient such as a mammal in need of such inhibition comprising the administration of an effective amount of the compound. The present invention is directed to the use of the compounds disclosed herein as inhibitors of dipeptidyl peptidase-IV enzyme activity.

In addition to primates, such as humans, a variety of other mammals can be treated according to the method of the present invention. For instance, mammals including, but not limited to, cows, sheep, goats, horses, dogs, cats, guinea pigs, rats or other bovine, ovine, equine, canine, feline, rodent or murine species can be treated. However, the method can also be practiced in other species, such as avian species (e.g., chickens).

The present invention is further directed to a method for the manufacture of a medicament for inhibiting dipeptidyl peptidase-IV enzyme activity in humans and animals comprising combining a compound of the present invention with a pharmaceutically acceptable carrier or diluent.

The subject treated in the present methods is generally a mammal, preferably a human being, male or female, in whom inhibition of dipeptidyl peptidase-IV enzyme activity is desired. The term "therapeutically effective amount" means the amount of the subject compound that will elicit the biological or medical response of a tissue, system, animal or human that is being sought by the researcher, veterinarian, medical doctor or other clinician.

The term "composition" as used herein is intended to encompass a product comprising the specified ingredients in the specified amounts, as well as any product which results, directly or indirectly, from combination of the specified ingredients in the specified amounts. Such term in relation to pharmaceutical composition, is intended to encompass a product comprising the active ingredient(s), and the inert ingredient(s) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing a compound of the present invention and a pharmaceutically acceptable carrier. By "pharmaceutically acceptable" it is meant the carrier, diluent or excipient must be compatible with the other ingredients of the formulation and not deleterious to the recipient thereof.

The terms "administration of" and or "administering a" compound should be understood to mean providing a compound of the invention or a prodrug of a compound of the invention to the individual in need of treatment.

The utility of the compounds in accordance with the present invention as inhibitors of dipeptidyl peptidase-IV enzyme activity may be demonstrated by methodology known in the art. Inhibition constants are determined as follows. A continuous fluorometric assay is employed with the substrate Gly-Pro-AMC, which is cleaved by DP-IV to release the fluorescent AMC leaving group. The kinetic parameters that describe this reaction are as follows: $K_m$=50 µM; $k_{cat}$=75 s$^{-1}$; $k_{cat}/K_m$=1.5×10$^6$ M$^{-1}$s$^{-1}$. A typical reaction contains approximately 50 pM enzyme, 50 µM Gly-Pro-AMC, and buffer (100 mM HEPES, pH 7.5, 0.1 mg/ml BSA) in a total reaction volume of 100 µl. Liberation of AMC is monitored continuously in a 96-well plate fluorometer using an excitation wavelength of 360 nm and an emission wavelength of 460 nm. Under these conditions, approximately 0.8 µM AMC is produced in 30 minutes at 25 degrees C. The enzyme used in these studies was soluble (transmembrane domain and cytoplasmic extension excluded) human protein produced in a baculovirus expression system (Bac-To-Bac, Gibco BRL). The kinetic constants for hydrolysis of Gly-Pro-AMC and GLP-1 were found to be in accord with literature values for the native enzyme. To measure the dissociation constants for compounds, solutions of inhibitor in DMSO were added to reactions containing enzyme and substrate (final DMSO concentration is 1%). All experiments were conducted at room temperature using the standard reaction conditions described above. To determine the dissociation constants ($K_i$), reaction rates were fit by non-linear regression to the Michaelis-Menton equation for competitive inhibition. The errors in reproducing the dissociation constants are typically less than two-fold.

In particular, the compounds of the following examples had activity in inhibiting the dipeptidyl peptidase-IV enzyme in the aforementioned assays, generally with an $IC_{50}$ of less than about 1 µM. Such a result is indicative of the intrinsic activity of the compounds in use as inhibitors the dipeptidyl peptidase-IV enzyme activity.

Dipeptidyl peptidase-IV enzyme (DP-IV) is a cell surface protein that has been implicated in a wide range of biological functions. It has a broad tissue distribution (intestine, kidney, liver, pancreas, placenta, thymus, spleen, epithelial cells, vascular endothelium, lymphoid and myeloid cells, serum), and distinct tissue and cell-type expression levels. DP-IV is identical to the T cell activation marker CD26, and it can cleave a number of immunoregulatory, endocrine, and neurological peptides in vitro. This has suggested a potential role for this peptidase in a variety of disease processes in humans or other species.

Accordingly, the subject compounds are useful in a method for the prevention or treatment of the following diseases, disorders and conditions.

Type II Diabetes and Related Disorders: It is well established that the incretins GLP-1 and GIP are rapidly inactivated in vivo by DP-IV. Studies with DP-IV$^{(-/-)}$-deficient mice and preliminary clinical trials indicate that DP-IV inhibition increases the steady state concentrations of GLP-1 and GIP, resulting in improved glucose tolerance. By analogy to GLP-1 and GIP, it is likely that other glucagon family peptides involved in glucose regulation are also inactivated by DP-IV (eg. PACAP). Inactivation of these peptides by DP-IV may also play a role in glucose homeostasis. The DP-IV inhibitors of the present invention therefore have utility in the treatment of type II diabetes and in the treatment and prevention of the numerous conditions that often accompany Type II diabetes, including metabolic syndrome X, reactive hypoglycemia, and diabetic dyslipidemia. Obesity, discussed below, is another condition that is often found with Type II diabetes that may respond to treatment with the compounds of this invention.

The following diseases, disorders and conditions are related to Type 2 diabetes, and therefore may be treated, controlled or in some cases prevented, by treatment with the compounds of this invention: (1) hyperglycemia, (2) low glucose tolerance, (3) insulin resistance, (4) obesity, (5) lipid disorders, (6) dyslipidemia, (7) hyperlipidemia, (8) hypertriglyceridemia, (9) hypercholesterolemia, (10) low HDL levels, (11) high LDL levels, (12) atherosclerosis and its sequelae, (13) vascular restenosis, (14) irritable bowel syndrome, (15) inflammatory bowel disease, including Crohn's disease and ulcerative colitis, (16) other inflammatory conditions, (17) pancreatitis, (18) abdominal obesity, (19) neurodegenerative disease, (20) retinopathy, (21) nephropathy, (22) neuropathy, (23) Syndrome X, (24) ovarian hyperandrogenism (polycystic ovarian syndrome), and other disorders where insulin resistance is a component.

Obesity: DP-IV inhibitors may be useful for the treatment of obesity. This is based on the observed inhibitory effects on food intake and gastric emptying of GLP-1 and GLP-2. Exogenous administration of GLP-1 in humans significantly decreases food intake and slows gastric emptying (*Am. J. Physiol.*, 277: R910-R916 (1999)). ICV administration of GLP-1 in rats and mice also has profound effects on food intake (*Nature Medicine*, 2: 1254-1258 (1996)). This inhibition of feeding is not observed in GLP-1R$^{(-/-)}$ mice, indicating that these effects are mediated through brain GLP-1 receptors. By analogy to GLP-1, it is likely that GLP-2 is also regulated by DP-IV. ICV administration of GLP-2 also inhibits food intake, analogous to the effects observed with GLP-1 (*Nature Medicine*, 6: 802-807 (2000)). In addition, studies with DP-IV deficient mice suggest that these animals are resistant to diet-induced obesity and associated pathology (e.g. hyperinsulinonemia).

Growth Hormone Deficiency: DP-IV inhibition may be useful for the treatment of growth hormone deficiency, based on the hypothesis that growth-hormone releasing factor (GRF), a peptide that stimulates release of growth hormone from the anterior pituitary, is cleaved by the DP-IV enzyme in vivo (WO 00/56297). The following data provide evidence that GRP is an endogenous substrate: (1) GRF is efficiently cleaved in vitro to generate the inactive product GRF[3-44] (*BBA* 1122: 147-153 (1992)); (2) GRF is rapidly degraded in plasma to GRF[3-44]; this is prevented by the DP-IV inhibitor diprotin A; and (3) GRF[3-44] is found in the plasma of a human GRF transgenic pig (*J. Clin. Invest.*, 83: 1533-1540 (1989)). Thus DP-IV inhibitors may be useful for the same spectrum of indications which have been considered for growth hormone secretagogues.

Intestinal Injury: The potential for using DP-IV inhibitors for the treatment of intestinal injury is suggested by the results of studies indicating that glucagon-like peptide-2 (GLP-2), a likely endogenous substrate for DP-IV, may exhibit trophic effects on the intestinal epithelium (*Regulatory Peptides*, 90: 27-32 (2000)). Administration of GLP-2 results in increased small bowel mass in rodents and attenuates intestinal injury in rodent models of colitis and enteritis.

Immunosuppression: DP-IV inhibition may be useful for modulation of the immune response, based upon studies implicating the DP-IV enzyme in T cell activation and in chemokine processing, and efficacy of DP-IV inhibitors in in vivo models of disease. DP-IV has been shown to be identical to CD26, a cell surface marker for activated immune cells. The expression of CD26 is regulated by the differentiation and activation status of immune cells. It is generally accepted that CD26 functions as a co-stimulatory molecule in in vitro models of T cell activation. A number of chemokines contain proline in the penultimate position, presumably to protect them from degradation by non-specific aminopeptidases. Many of these have been shown to be processed in vitro by DP-IV. In several cases (RANTES, LD78-beta, MDC, eotaxin, SDF-1alpha), cleavage results in an altered activity in chemotaxis and signaling assays. Receptor selectivity also appears to be modified in some cases (RANTES). Multiple N-terminally truncated forms of a number of chemolines have been identified in in vitro cell culture systems, including the predicted products of DP-IV hydrolysis.

DP-IV inhibitors have been shown to be efficacious immunosuppressants in animal models of transplantation and arthritis. Prodipine (Pro-Pro-diphenyl-phosphonate), an irreversible inhibitor of DP-IV, was shown to double cardiac allograft survival in rats from day 7 to day 14 (*Transplantation*, 63: 1495-1500 (1997)). DP-IV inhibitors have been tested in collagen and alkyldiamine-induced arthritis in rats and showed a statistically significant attenuation of hind paw swelling in this model [*Int. J. Immunopharmacology*, 19:15-24 (1997) and *Immunopharmacology*, 40: 21-26 (1998)]. DP-IV is upregulated in a number of autoimmune diseases including rheumatoid arthritis, multiple sclerosis, Graves' disease, and Hashimoto's thyroiditis (*Immunology Today*, 20: 367-375 (1999)).

HIV Infection: DP-IV inhibition may be useful for the treatment or prevention of HIV infection or AIDS because a number of chemokines which inhibit HIV cell entry are potential substrates for DP-IV (*Immunology Today* 20: 367-375 (1999)). In the case of SDF-1alpha, cleavage decreases antiviral activity (*PNAS*, 95: 6331-6 (1998)). Thus, stabilization of SDP-1alpha through inhibition of DP-IV would be expected to decrease HIV infectivity.

Hematopoiesis: DP-IV inhibition may be useful for the treatment or prevention of hematopiesis because DP-IV may be involved in hematopoiesis. A DP-IV inhibitor, Val-Boro-Pro, stimulated hematopoiesis in a mouse model of cyclophosphamide-induced neutropenia (WO 99/56753).

Neuronal Disorders: DP-IV inhibition may be useful for the treatment or prevention of various neuronal or psychiatric disorders because a number of peptides implicated in a variety of neuronal processes are cleaved in vitro by DP-IV. A DP-IV inhibitor thus may have a therapeutic benefit in the treatment of neuronal disorders. Endomorphin-2, beta-casomorphin, and substance P have all been shown to be in vitro substrates for DP-IV. In all cases, in vitro cleavage is highly efficient, with $k_{cat}/K_m$ about $10^6$ $M^{-1}s^{-1}$ or greater. In an electric shock jump test model of analgesia in rats, a DP-IV inhibitor showed a significant effect that was independent of the presence of exogenous endomorphin-2 (*Brain Research*, 815: 278-286 (1999)).

Neuroprotective and neuroregenerative effects of DP-IV inhibitors were also evidenced by the inhibitors' ability to protect motor neurons from excitotoxic cell death, to protect striatal innervation of dopaminergic neurons when administered concurrently with MPTP, and to promote recovery of striatal innervation density when given in a therapeutic manner following MPTP treatment [see Yong-Q. Wu, et al., "Neuroprotective Effects of Inhibitors of Dipeptidyl Peptidase-IV In Vitro and In Vivo," *Int. Conf. On Dipeptidyl Aminopeptidases: Basic Science and Clinical Applications*, Sep. 26-29, 2002 (Berlin, Germany)].

Tumor Invasion and Metastasis: DP-IV inhibition may be useful for the treatment or prevention of tumor invasion and metastasis because an increase or decrease in expression of several ectopeptidases including DP-IV has been observed during the transformation of normal cells to a malignant phenotype (*J. Exp. Med.*, 190: 301-305 (1999)). Up- or down-regulation of these proteins appears to be tissue and cell-type specific. For example, increased CD26/DP-IV expression has been observed on T cell lymphoma, T cell acute lymphoblastic leukemia, cell-derived thyroid carcinomas, basal cell carcinomas, and breast carcinomas. Thus, DP-IV inhibitors may have utility in the treatment of such carcinomas.

Benign Prostatic Hypertrophy: DP-IV inhibition may be useful for the treatment of benign prostatic hypertrophy because increased DP-IV activity was noted in prostate tissue from patients with BPH (*Eur. J. Clin. Chem. Clin. Biochem.*, 30: 333-338 (1992)).

Sperm Motility/Male Contraception: DP-IV inhibition may be useful for the altering sperm motility and for male contraception because in seminal fluid, prostatosomes, prostate derived organelles important for sperm motility, possess very high levels of DP-IV activity (*Eur. J. Clin. Chem. Clin. Biochem.*, 30: 333-338 (1992)).

Gingivitis: DP-IV inhibition may be useful for the treatment of gingivitis because DP-IV activity was found in gingival crevicular fluid and in some studies correlated with periodontal disease severity (*Arch. Oral Biol.*, 37: 167-173 (1992)).

Osteoporosis: DP-IV inhibition may be useful for the treatment or prevention of osteoporosis because GIP receptors are present in osteoblasts.

The compounds of the present invention have utility in treating or preventing one or more of the following conditions or diseases: (1) hyperglycemia, (2) low glucose tolerance, (3) insulin resistance, (4) obesity, (5) lipid disorders, (6) dyslipidernia, (7) hyperlipidemia, (8) hypertriglyceridemnia, (9) hypercholesterolemia, (10) low HDL levels, (11) high LDL levels, (12) atherosclerosis and its sequelae, (13) vascular restenosis, (14) irritable bowel syndrome, (15) inflammatory bowel disease, including Crohn's disease and ulcerative colitis, (16) other inflammatory conditions, (17) pancreatitis, (18) abdominal obesity, (19) neurodegenerative disease, (20) retinopathy, (21) nephropathy, (22) neuropathy, (23) Syndrome X, (24) ovarian hyperandrogenism (polycystic ovarian syndrome), (25) Type II diabetes, (26) growth hormone deficiency, (27) neutropenia, (28) neuronal disorders, (29) tumor metastasis, (30) benign prostatic hypertrophy, (32) gingivitis, (33) hypertension, (34) osteoporosis, and other conditions that may be treated or prevented by inhibition of DP-IV.

The subject compounds are further useful in a method for the prevention or treatment of the aforementioned diseases, disorders and conditions in combination with other agents.

The compounds of the present invention may be used in combination with one or more other drugs in the treatment, prevention, suppression or amelioration of diseases or conditions for which compounds of Formula I or the other drugs may have utility, where the combination of the drugs together are safer or more effective than either drug alone. Such other drug(s) may be administered, by a route and in an amount commonly used therefor, contemporaneously or sequentially with a compound of Formula I. When a compound of Formula I is used contemporaneously with one or more other drugs, a pharmaceutical composition in unit dosage form containing such other drugs and the compound of Formula I is preferred. However, the combination therapy may also include therapies in which the compound of Formula I and one or more other drugs are administered on different overlapping schedules. It is also contemplated that when used in combination with one or more other active ingredients, the compounds of the present invention and the other active ingredients may be used in lower doses than when each is used singly. Accordingly, the pharmaceutical compositions of the present invention include those that contain one or more other active ingredients, in addition to a compound of Formula I.

Examples of other active ingredients that may be administered in combination with a compound of Formula I, and either administered separately or in the same pharmaceutical composition, include, but are not limited to:

(a) other dipeptidyl peptidase IV (DP-IV) inhibitors;

(b) insulin sensitizers including (i) PPARγ agonists such as the glitazones (e.g. troglitazone, pioglitazone, englitazone, MCC-555, rosiglitazone, and the like) and other PPAR ligands, including PPARα/γ dual agonists, such as KRP-297, and PPARα agonists such as fenofibric acid derivatives (gemfibrozil, clofibrate, fenofibrate and bezafibrate), (ii) biguanides such as metformin and phenformin, and (iii) protein tyrosine phosphatase-1B (PTP-1B) inhibitors;

(c) insulin or insulin mimetics;

(d) sulfonylureas and other insulin secretagogues, such as tolbutamide glyburide, glipizide, glimepiride, and meglitinides, such as repaglinide;

(e) α-glucosidase inhibitors (such as acarbose and miglitol);

(f) glucagon receptor antagonists such as those disclosed in WO 98/04528, WO 99/01423, WO 00/39088, and WO 00/69810;

(g) GLP-1, GLP-1 mimetics, and GLP-1 receptor agonists such as those disclosed in WO00/42026 and WO00/59887;

(h) GIP and GIP mimetics such as those disclosed in WO00/58360, and GIP receptor agonists;

(i) PACAP, PACAP mimetics, and PACAP receptor agonists such as those disclosed in WO 01/23420;

(j) cholesterol lowering agents such as (i) HMG-CoA reductase inhibitors (lovastatin, simvastatin, pravastatin, cerivastatin, fluvastatin, atorvastatin, itavastatin, and rosuvastatin, and other statins), (ii) sequestrants (cholestyramine, colestipol, and dialkylaminoalkyl derivatives of a cross-linked dextran), (iii) nicotinyl alcohol, nicotinic acid or a salt thereof, (iv) PPARα agonists such as fenofibric acid derivatives (gemfibrozil, clofibrate, fenofibrate and bezafibrate), (v) PPARα/γ dual agonists, such as KRP-297, (vi) inhibitors of cholesterol absorption, such as beta-sitosterol and ezetimibe, (vii) acyl CoA:cholesterol acyltransferase inhibitors, such as avasimibe, and (viii) anti-oxidants, such as probucol;

(k) PPARδ agonists, such as those disclosed in WO97/28149;

(l) antiobesity compounds such as fenfluramine, dexfenfluramine, phentermine, sibutramine, orlistat, neuropeptide $Y_1$ or $Y_5$ antagonists, CB1 receptor inverse agonists and antagonists, $β_3$ adrenergic receptor agonists, melanocortin-receptor agonists, in particular melanocortin-4 receptor agonists, ghrelin antagonists, and melanin-concentrating hormone (MCH) receptor antagonists;

(m) ileal bile acid transporter inhibitors;

(n) agents intended for use in inflammatory conditions such as aspirin, non-steroidal anti-inflammatory drugs, glucocorticoids, azulfidine, and selective cyclooxygenase-2 inhibitors; and (o) antihypertensive agents such as ACE inhibitors (enalapril, lisinopril, captopril, quinapril, tandolapril), A-II receptor blockers (losartan, candesartan, irbesartan, valsartan, telmisartan, eprosartan), beta blockers and calcium channel blockers.

Dipeptidyl peptidase-IV inhibitors that can be combined with compounds of structural formula I include those disclosed in WO 03/004498 (16 Jan. 2003); WO 03/004496 (16 Jan. 2003); EP 1 258 476 (20 Nov. 2002); WO 02/083128 (24 Oct. 2002); WO 02/062764 (15 Aug. 2002); WO 03/000250 (3 Jan. 2003); WO 03/002530 (9 Jan. 2003); WO 03/002531 (9 Jan. 2003); WO 03/002553 (9 Jan. 2003); WO 03/002593 (9 Jan. 2003); WO 03/000180 (3 Jan. 2003); and WO 03/000181 (3 Jan. 2003). Specific DP-IV inhibitor compounds include isoleucine thiazolidide; NVP-DPP728; P32/98; and LAF 237.

Antiobesity compounds that can be combined with compounds of structural formula I include fenfluramine, dexfenfluranine, phentermine, sibutramine, orlistat, neuropeptide $Y_1$ or $Y_5$ antagonists, cannabinoid CB1 receptor antagonists or inverse agonists, melanocortin receptor agonists, in particular, melanocortin-4 receptor agonists, ghrelin antagonists, and melanin-concentrating hormone (MCH) receptor antagonists. For a review of anti-obesity compounds that can be combined with compounds of structural formula I, see S. Chaki et al., "Recent advances in feeding suppressing agents: potential therapeutic strategy for the treatment of obesity," *Expert Opin. Ther. Patents*, 11: 1677-1692 (2001) and D. Spanswick and K. Lee, "Emerging antiobesity drugs," *Expert Opin. Emerging Drugs*, 8:217-237 (2003).

Neuropeptide Y5 antagonists that can be combined with compounds of structural formula I include those disclosed in U.S. Pat. No. 6,335,345 (1 Jan. 2002) and WO 01/14376 (1 Mar. 2001); and specific compounds identified as GW 59884A; GW 569180A; LY366377; and CGP-71683A.

Cannabinoid CB1 receptor antagonists that can be combined with compounds of formula I include those disclosed in PCT Publication WO 03/007887; U.S. Pat. No. 5,624,941, such as rimonabant; PCT Publication WO 02/076949, such as SLV-319; U.S. Pat. No. 6,028,084; PCT Publication WO 98/41519; PCT Publication WO 00/10968; PCT Publication WO 99/02499; U.S. Pat. No. 5,532,237; and U.S. Pat. No. 5,292,736.

Melanocortin receptor agonists that can be combined with compounds of structural formula I include those disclosed in WO 03/009847 (6 Feb. 2003); WO 02/068388 (6 Sep. 2002); WO 99/64002 (16 Dec. 1999); WO 00/74679 (14 Dec. 2000); WO 01/70708 (27 Sep. 2001); and WO 01/70337 (27 Sep. 2001) as well as those disclosed in J. D. Speake et al., "Recent advances in the development of melanocortin-4 receptor agonists," *Expert Opin. Ther. Patents*, 12: 1631-1638 (2002).

When a compound of the present invention is used contemporaneously with one or more other drugs, a pharmaceutical composition containing such other drugs in addition to the compound of the present invention is preferred. Accordingly, the pharmaceutical compositions of the present invention include those that also contain one or more other active ingredients, in addition to a compound of the present invention.

The weight ratio of the compound of the present invention to the second active ingredient may be varied and will depend upon the effective dose of each ingredient. Generally, an effective dose of each will be used. Thus, for example, when a compound of the present invention is combined-with another agent, the weight ratio of the compound of the present invention to the other agent will generally range from about 1000:1 to about 1:1000, preferably about 200:1 to about 1:200. Combinations of a compound of the present invention and other active ingredients will generally also be within the aforementioned range, but in each case, an effective dose of each active ingredient should be used.

In such combinations the compound of the present invention and other active agents may be administered separately or in conjunction. In addition, the administration of one element may be prior to, concurrent to, or subsequent to the administration of other agent(s).

The compounds of the present invention may be administered by oral, parenteral (e.g., intramuscular, intraperitoneal, intravenous, ICV, intracisternal injection or infusion, subcutaneous injection, or implant), by inhalation spray, nasal, vaginal, rectal, sublingual, or topical routes of administration and may be formulated, alone or together, in suitable dosage unit formulations containing conventional non-toxic pharmaceutically acceptable carriers, adjuvants and vehicles appropriate for each route of administration. In addition to the treatment of warm-blooded animals such as mice, rats, horses, cattle, sheep, dogs, cats, monkeys, etc., the compounds of the invention are effective for use in humans.

The pharmaceutical compositions for the administration of the compounds of this invention may conveniently be presented in dosage unit form and may be prepared by any of the methods well known in the art of pharmacy. AU methods include the step of bringing the active ingredient into association with the carrier which constitutes one or more accessory ingredients. In general, the pharmaceutical compositions are prepared by uniformly and intimately bringing the active ingredient into association with a liquid carrier or a finely divided solid carrier or both, and then, if necessary, shaping the product into the desired formulation. In the pharmaceutical composition the active object compound is included in an amount sufficient to produce the desired effect upon the process or condition of diseases. As used herein, the term "composition" is intended to encompass a product comprising the specified ingredients in the specified amounts, as well as any product which results, directly or indirectly, from combination of the specified ingredients in the specified amounts.

The pharmaceutical compositions containing the active ingredient may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the techniques described in the U.S. Pat. Nos. 4,256,108; 4,166,452; and 4,265,874 to form osmotic therapeutic tablets for control release.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin, or olive oil.

Aqueous suspensions contain the active materials in admixture with excipients suitable for the manufacture of aqueous suspensions. Such excipients are suspending agents, for example sodium carboxymethylcellulose, methylcellulose, hydroxy-propylmethylcellulose, sodium alginate, polyvinyl-pyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl, p-hydroxybenzoate, one or more coloring agents, one or more flavoring agents, and one or more sweetening agents, such as sucrose or saccharin.

Oily suspensions may be formulated by suspending the active ingredient in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

The pharmaceutical compositions of the invention may also be in the form of oil-in-water emulsions. The oily phase may be a vegetable oil, for example olive oil or arachis oil, or a mineral oil, for example liquid paraffin or mixtures of these. Suitable emulsifying agents may be naturally-occurring gums, for example gum acacia or gum tragacanth, naturally-occuring phosphatides, for example soy bean, lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative and flavoring and coloring agents.

The pharmaceutical compositions may be in the form of a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The compounds of the present invention may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols.

For topical use, creams, ointments, jellies, solutions or suspensions, etc., containing the compounds of the present invention are employed. (For purposes of this application, topical application shall include mouthwashes and gargles.)

The pharmaceutical composition and method of the present invention may further comprise other therapeutically active compounds as noted herein which are usually applied in the treatment of the above mentioned pathological conditions.

In the treatment or prevention of conditions which require inhibition of dipeptidyl peptidase-IV enzyme activity an appropriate dosage level will generally be about 0.01 to 500 mg per kg patient body weight per day which can be administered in single or multiple doses. Preferably, the dosage level will be about 0.1 to about 250 mg/kg per day; more preferably about 0.5 to about 100 mg/kg per day. A suitable dosage level may be about 0.01 to 250 mg/kg per day, about 0.05 to 100 mg/kg per day, or about 0.1 to 50 mg/kg per day. Within this range the dosage may be 0.05 to 0.5, 0.5 to 5 or 5 to 50 mg/kg per day. For oral administration, the compositions are preferably provided in the form of tablets containing 1.0 to 1000 mg of the active ingredient, particularly 1.0, 5.0, 10.0, 15.0, 20.0, 25.0, 50.0, 75.0, 100.0, 150.0, 200.0, 250.0, 300.0, 400.0, 500.0, 600.0, 750.0, 800.0, 900.0, and 1000.0 mg of the active ingredient for the symptomatic adjustment of the dosage to the patient to be treated. The compounds may be administered on a regimen of 1 to 4 times per day, preferably once or twice per day.

When treating or preventing diabetes mellitus and/or hyperglycemia or hypertriglyceridemia or other diseases for which compounds of the present invention are indicated, generally satisfactory results are obtained when the compounds of the present invention are administered at a daily dosage of from about 0.1 mg to about 100 mg per kilogram of animal body weight, preferably given as a single daily dose or in divided doses two to six times a day, or in sustained release form For most large mammals, the total daily dosage is from about 1.0 mg to about 1000 mg, preferably from about 1 mg to about 50 mg. In the case of a 70 kg adult human, the total daily dose will generally be from about 7 mg to about 350 mg. This dosage regimen may be adjusted to provide the optimal therapeutic response.

It will be understood, however, that the specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

Several methods for preparing the compounds of this invention are illustrated in the following Schemes and Examples. Starting materials are made according to procedures known in the art or as illustrated herein.

SCHEME 1

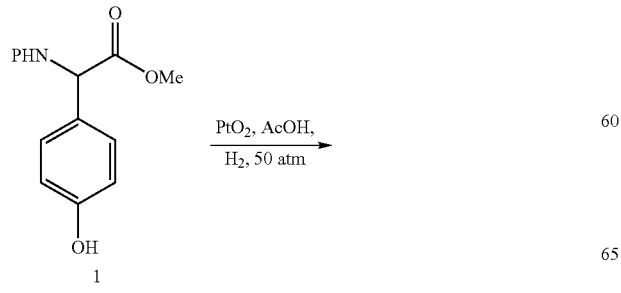

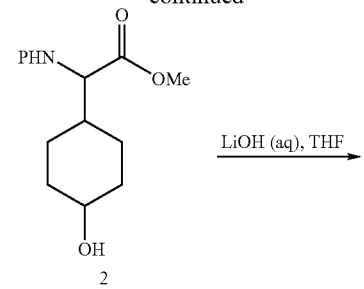

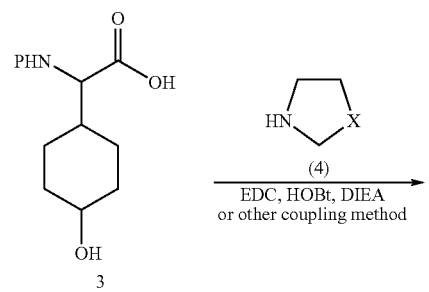

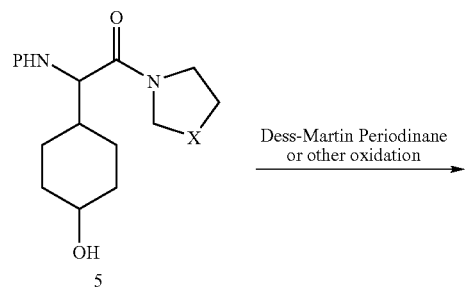

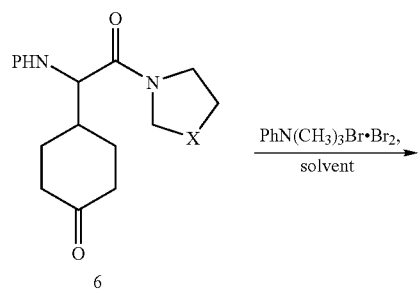

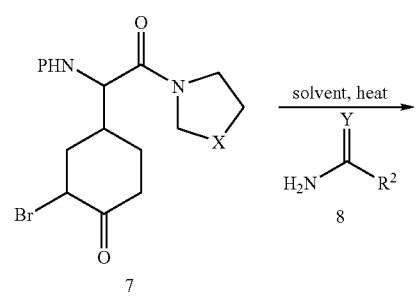

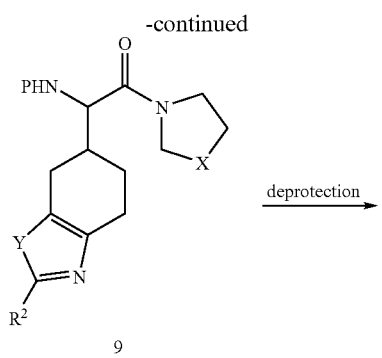

9

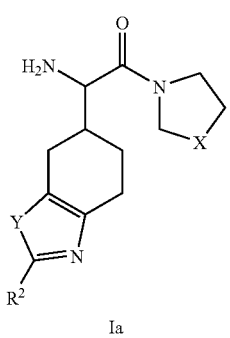

Ia

The preparation of Compounds of formula Ia, wherein $R^1$ is hydrogen and Z is nitrogen, is illustrated in Scheme 1. Ester 1, which may be commercially available or readily prepared from the corresponding amino acid by protection using, for example di-tert-butyl dicarbonate (for P=Boc), and esterification in methanol or ethanol containing an acid such as hydrochloric acid, is subjected to catalytic hydrogenation using a catalyst such as platinum oxide in a solvent such as acetic acid at a pressure of up to 50 psi for a time of 2 to 16 h to the give cyclohexyl analog 2. The ester functionality in compound 2 can be removed to yield the carboxylic acid 3. In the case of an ester such as methyl or ethyl, this is achieved by saponification using a base such as aqueous lithium hydroxide in a polar solvent such as tetrahydrofuran, methanol or a mixture of similar solvents. Acid 3 is coupled to heterocyclic amine 4 under standard peptide coupling conditions, for example, using 1-ethyl-3-(3-dimethylaminopropyl)-carbodiinide (EDC), 1-hydroxybenzotriazole (HOBT), and a base, generally N,N-diisopropylethylamine, in a solvent such as N,N-dimethylformamide (DMF) or dichloromethane for 3 to 48 h at ambient temperature to provide intermediate 5. The resultant alcohol may be oxidized to the ketone using, for example, the Dess-Martin periodinane reagent in dichloromethane for 1 to 5 h at ambient temperature to provide intermediate 6. The protected ketone 6 is treated with phenyltrimethylammonium perbromide in a solvent such as THF for 5-20 hours at ambient temperature to afford intermediate 7.

α-Bromoketone 7 may then be treated with a primary amide, a primary thioamide, or a primary amidine 8 in a solvent such as DMF for 3 to 48 h at elevated temparature to provide intermediate 9 (Y=O, S, or N, respectively). When P=Boc, heterocycle 9 may be deprotected either by stiring the compounds with an acid such as TFA or HCl in a solvent such as dichloromethane or dioxane at ambient temperature for 0.5 to 3 h. When P=Cbz, 9 may be deprotected with iodotrimethylsilane in a solvent such as acetonitrile for 0.5 to 2 h at 0° C. or at ambient temperature. Deprotection of 9 affords the final compound Ia, wherein $R^1$ is hydrogen. The product is purified from unwanted side products, if necessary, by recrystallization, trituration, preparative thin layer chromatography, flash chromatography on silica gel, such as with a Biotage® apparatus, or reverse phase HPLC. Compounds that are purified by HPLC may be isolated as the corresponding salt. Diastereomeric mixtures may be resolved using a ChiralCel column (types AD, AS, OD, or OJ). Purification of intermediates is achieved in the same manner. As will be understood by those skilled in the art, for the preparation of enantiomerically pure compounds of formula Ia, enantiomerically pure alpha amino acids 1 may be used. Related routes to these compounds can be found in the following references: Nutt et al., Peptides: Structure and Function, *Proceed. of the 9th Amer. Pept. Symp.*, eds C. Deber et al., Pierce Chemical Co. Rockford, Ill., 441 (1985), and Banfi et al., *Syn. Commun.*, 19, 1787-1799 (1989).

Primary amides, primary thioamides, or primary amidines 8 are commercially available, known in the literature, or may be prepared by a variety of methods commonly known to those skilled in the art.

SCHEME 2

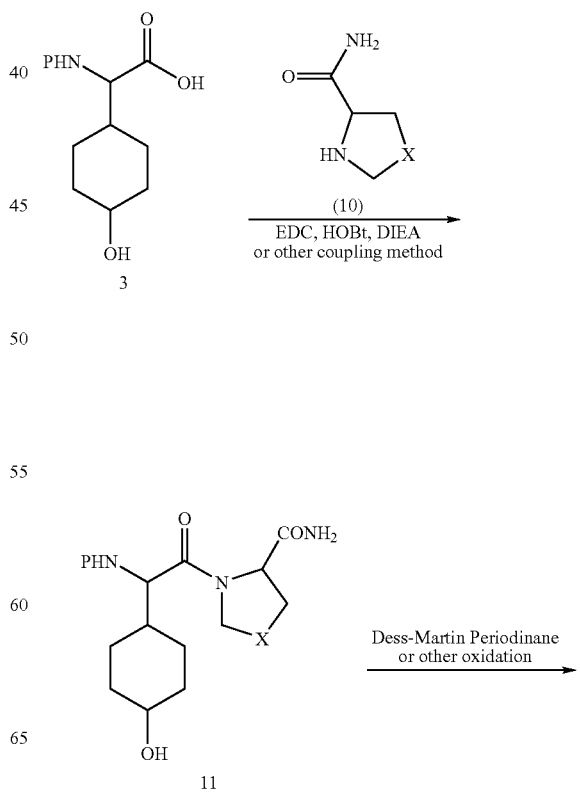

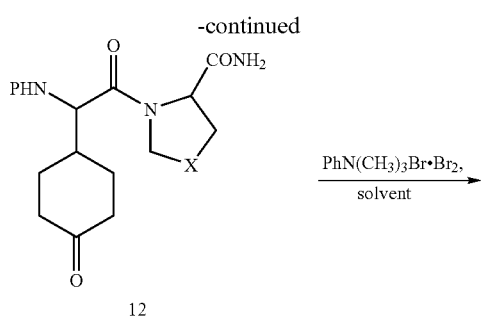
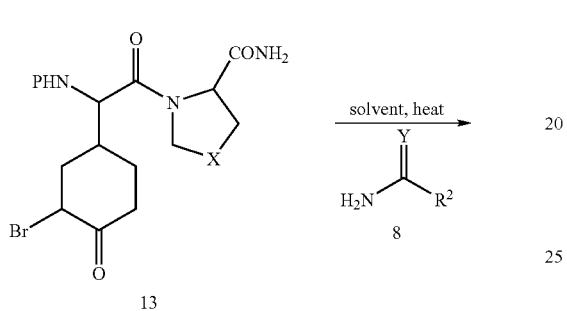

ally N,N-diisopropylethylamine, in a solvent such as N,N-dimethylformamide (DMF) or dichloromethane for 3 to 48 h at ambient temperature to provide intermediate 11. Intermediate 11 is converted to the protected heterocycle 14 as described above for Scheme 1. Heterocycle 14 is then treated with a dehydrating agent such as cyanuric chloride in a polar solvent, for example, dimethylformamide for 1 to 16 h at 0 to 50° C. to provide the nitrile. The protecting group is then removed with, for example, trifluoroacetic acid in dichloromethane to give the desired product Ib.

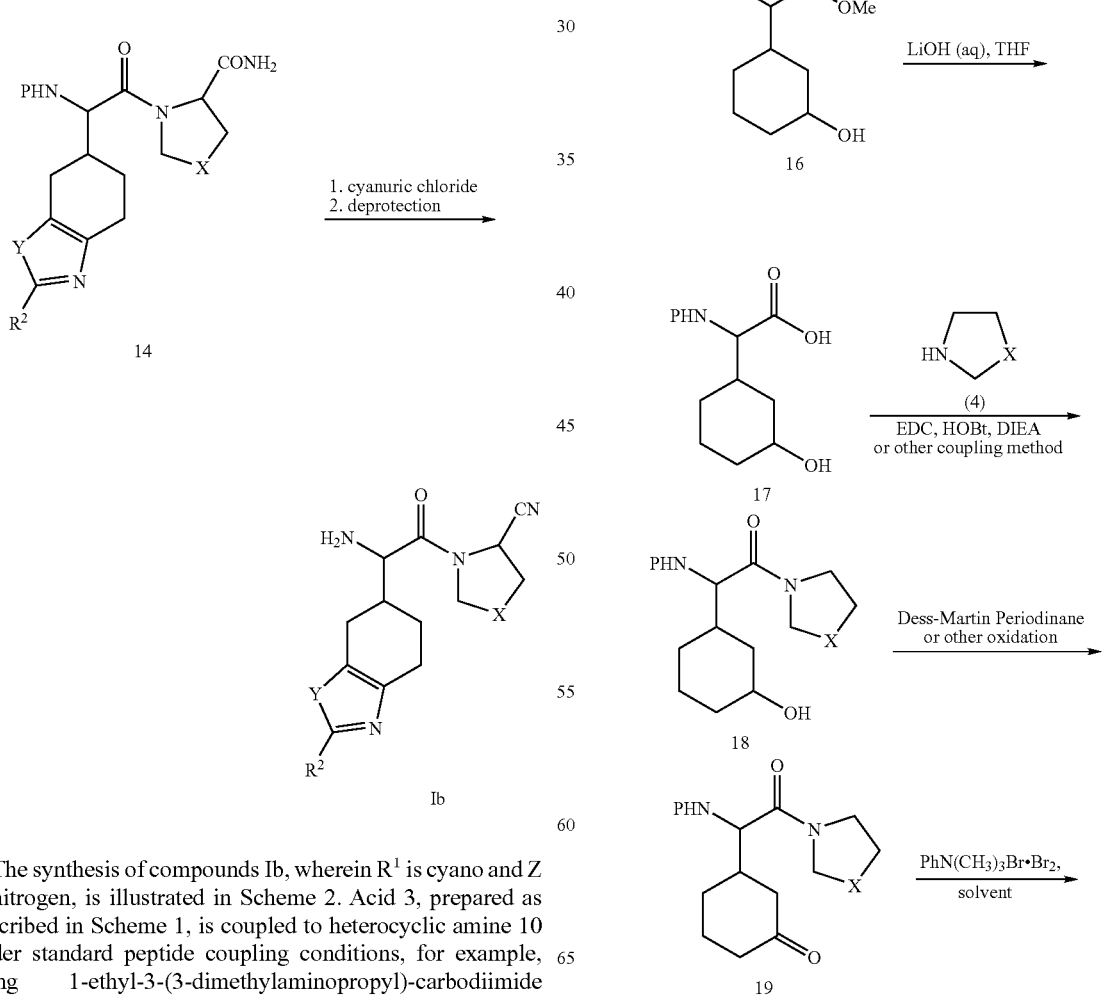

The synthesis of compounds Ib, wherein $R^1$ is cyano and Z is nitrogen, is illustrated in Scheme 2. Acid 3, prepared as described in Scheme 1, is coupled to heterocyclic amine 10 under standard peptide coupling conditions, for example, using 1-ethyl-3-(3-dimethylaminopropyl)-carbodiimide (EDC), 1-hydroxybenzotriazole (HOBT), and a base, gener-

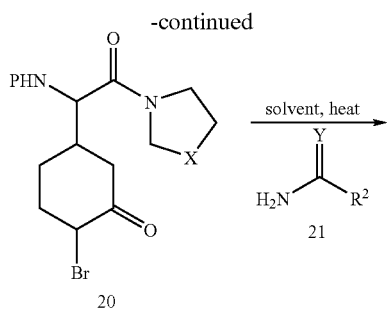

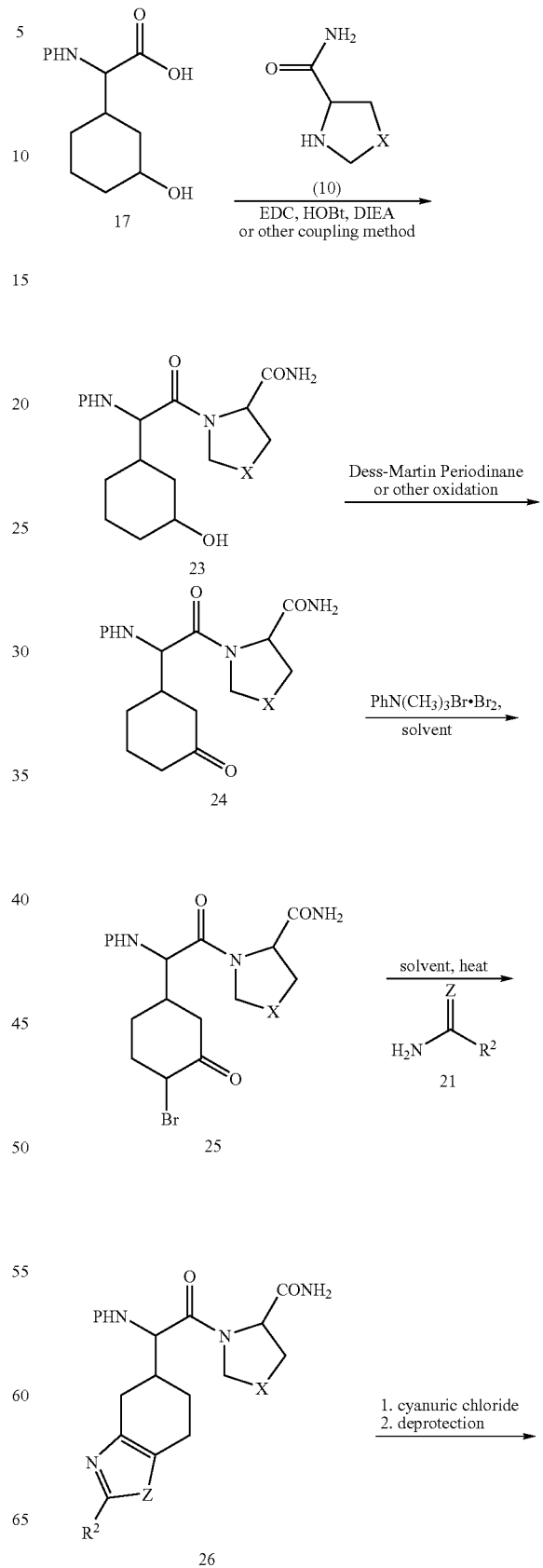

SCHEME 4

The synthesis of compounds Ic, wherein R¹ is hydrogen and Y is nitrogen, is illustrated in Scheme 3. Ester 15, which may be commercially available or readily prepared from the corresponding amino acid by protection using, for example di-tert-butyl dicarbonate (for P=Boc), and esterification in methanol or ethanol containing an acid such as hydrochloric acid, is subjected to catalytic hydrogenation using a catalyst such as platinum oxide in a solvent such as acetic acid at a pressure of up to 50 psi for a time of 2 to 16 h to the give cyclohexyl analog 16. Intermediate 16 is converted to the desired heterocycle Ic as described above for Scheme 1. As will be understood by those skilled in the art, for the preparation of enantiomerically pure alpha compounds of formula Ic, enantiomerically pure alpha amino acids 15 may be used. Related routes to these compounds can be found in the following references: Nutt et al., Peptides: Structure and Function, *Proceed. of the 9th Amer. Pept. Symp.*, eds C. Deber et al., Pierce Chemical Co. Rockford, Ill., 441 (1985), and Banfi et al., *Syn. Commun.*, 19, 1787-1799 (1989).

Primary amides, primary thioamides, or primary amidines 21 are commercially available, known in the literature, or may be prepared by a variety of methods commonly known to those skilled in the art.

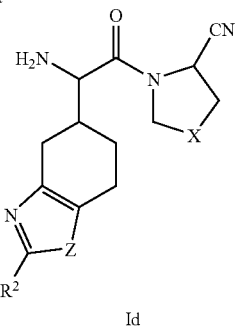

The synthesis of compounds Id, wherein $R^1$ is cyano and Y is nitrogen, is illustrated in Scheme 4. Acid 17, prepared as described in Scheme 3, is converted to the heterocycle Id as described above for Scheme 2.

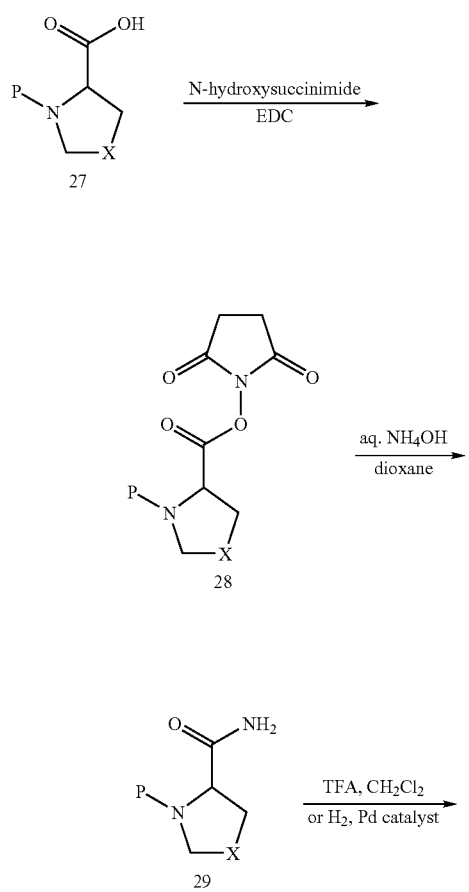

Heterocycles 10 are commercially available, known in the literature or may be conveniently prepared by a variety of methods familiar to those skilled in the art. One common route is illustrated in Scheme 5 and involves treatment of acid 27, wherein P is a carbamate protecting group such as Boc or Cbz, with N-hydroxysuccinimide and EDC or other suitable coupling agent in a solvent such as dichloromethane for 1 to 16 h. The resultant product 28 is then treated with aqueous ammonium hydroxide in a solvent such as dioxane. Removal of the protecting group, for example by treatment with TFA in dichloromethane in the case of Boc or under catalytic hydrogenation conditions in the case of Cbz, provides intermediates 10. Acid derivatives 27 are commercially available, known in the literature or may be conveniently prepared by a variety of methods familiar to those skilled in the art. For example, when X is CHF or $CF_2$, synthesis of the methyl ester of 27 is described in Demange et. al., *Tetrahedron Lett.*, 39, 1169, (1998).

In some cases the product I or synthetic intermediates illustrated in the above schemes may be further modified, for example, by manipulation of substituents on $R^2$ or $R^7$. These manipulations may include, but are not limited to, substitution, reduction, oxidation, alkylation, acylation, and hydrolysis reactions which are commonly known to those skilled in the art.

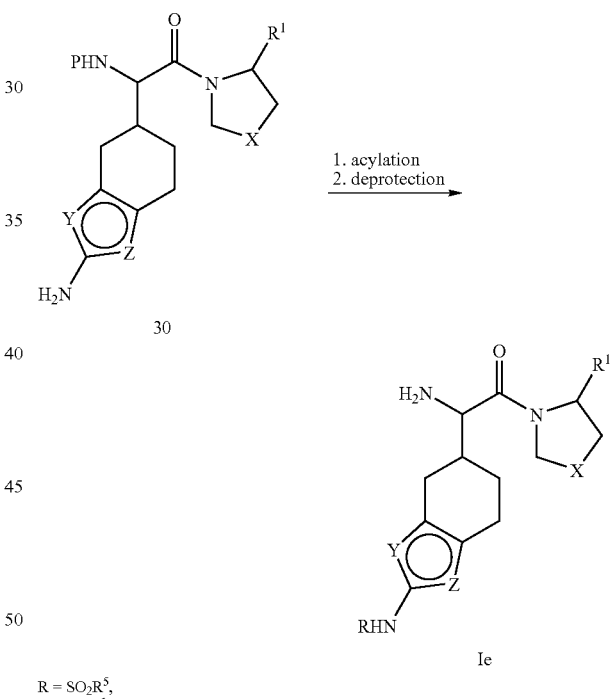

One such manipulation is illustrated in Scheme 6, wherein aminoheterocycle 30 is acylated with, for example, an acid chloride, an activated carboxylic acid, or a sulfonyl chloride in the presence of a base such as pyridine or N,N-diisopropylethylamine, in a solvent such as N,N-dimethylformamide (DMF) or dichloromethane for 3 to 48 h at ambient temperature to provide the R substituted aminoheterocycle. Removal of the protecting group, for example by treatment with TFA in dichloromethane in the case of Boc or with iodotrimethylsilane in acetonitrile in the case of Cbz, provides final compounds of formula Ie.

SCHEME 7

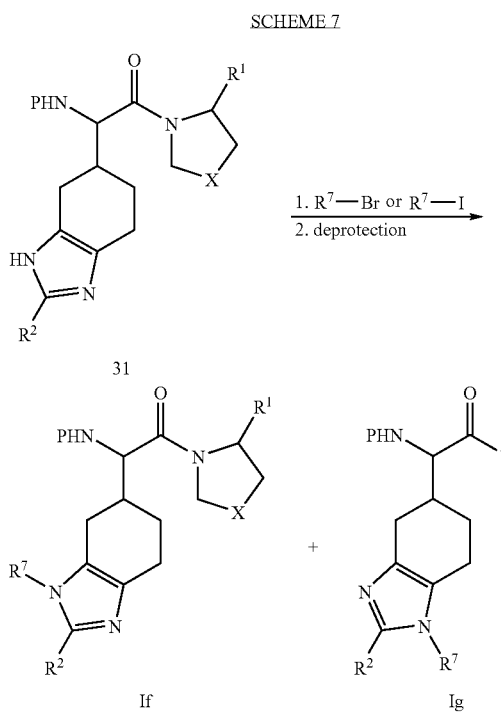

Another such example is illustrated in Scheme 7. Intermediate 31, wherein Y and Z are N and N—H, is treated with an alkyl halide such as an alkyl bromide or alkyl iodide. Deprotection affords the product, typically as a mixture of isomers, If and Ig.

In some cases the order of carrying out the foregoing reaction schemes may be varied to facilitate the reaction or to avoid unwanted reaction products. The following examples are provided so that the invention might be more fully understood. These examples are illustrative only and should not be construed as limiting the invention in any way.

INTERMEDIATE 1

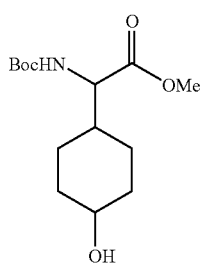

Methyl (2S)-[(tert-butoxycarbonyl)amino](4-hydroxycyclohexyl)ethanoate

To a solution of 20 mL (230 mmol) of acetyl chloride in 400 mL of methanol at 0° C. was added 20 g (120 mmol) of (S)-4-hydroxyphenylglycine. The mixture was stirred at ambient temperature for 16 h, heated at 40° C. for 2 h, cooled and concentrated in vacuo. Water was added and the mixture was extracted with three portions of dichloromethane. The combined organic phase was washed with brine, dried over magnesium sulfate, and concentrated in vacuo to give the crude methyl ester. This material was dissolved in 400 mL of dichloromethane, and 28.8 g (132 mmol) of di-tert-butyl dicarbonate and 31.4 mL (180 mmol) of N,N-diisopropylethylamine (DIEA) were added. The mixture was stirred at ambient temperature for 20 h, concentrated in vacuo, and dissolved in 400 mL of ethyl acetate. The organic phase was washed sequentially with saturated sodium bicarbonate solution, water, and brine, dried over magnesium sulfate, and concentrated in vacuo. The crude solid was triturated with 200 mL of 1:4 ether:hexane to give 30 g of the Boc carbamate which was dissolved in 300 mL of acetic acid. To the solution was added 2.2 g of platinum (IV) oxide and the reaction was shaken under an atmosphere of hydrogen (48 psi) for 2 h, filtered and concentrated in vacuo. The crude material was dissolved in ethyl acetate and washed sequentially with saturated sodium bicarbonate solution, water, and brine, dried over magnesium sulfate, and concentrated in vacuo. Purification by flash chromatography (silica gel, 20 to 40% ethyl acetate in hexanes) afforded the cis title compound. $^1$H NMR (400 MHz, CDCl$_3$) δ 5.05 (bd, 1H, J=12 Hz), 4.33-4.27 (m, 1H), 4.05 (bs, 1H), 3.78 (s, 3H), 1.89-1.78 (m, 2H), 1.63-1.38 (m, 16H). Continued elution gave the trans title compound. $^1$H NMR (400 MHz, CDCl$_3$) δ 5.04 (bd, 1H, J=12 Hz), 4.30-4.23 (m, 1H), 3.78 (s, 3H), 3.59-3.51 (m, 1H), 2.08-2.00 (m, 2H), 1.79-1.50 (m, 3H), 1.43 (s, 9H), 1.33-1.04 (m, 4H).

INTERMEDIATE 2

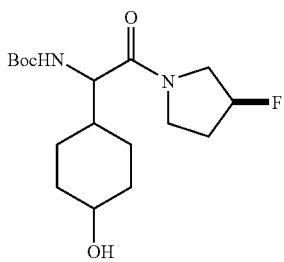

tert-Butyl [2-[(3S)-3-fluoropyrrolidin-1-yl]-1-(4-hydroxycyclohexyl)-2-oxoethyl]carbamate To a solution of 10 g (35 mmol) of Intermediate 1 in 525 mL of THF and 175 mL of methanol was added 174 mL (174 mmol) of 1 N aqueous lithium hydroxide solution. The reaction mixture was stirred for 2 h at ambient temperature, then concentrated in vacuo. The residue was acidified with 400 mL of 5% aqueous hydrochloric acid and the mixture extracted with two 400 mL portions of ethyl acetate. The combined organic extracts were washed sequentially with 500 mL of 5% aqueous hydrochloric acid and 500 mL of brine, dried over sodium sulfate, filtered and concentrated in vacuo. A 2.5 g sample (9.1 mmol) of the crude acid was dissolved in 100 mL of dichloromethane and 978 mg (11 mmol) of (S)-2-fluoropyrrolidine hydrochloride (1.8 g, 9.6 mmol), EDC (1.2 g, 9.2 mmol), HOBt (1.2 g, 9.2 mmol) and DIEA (1.7 mL, 9.6 mmol) were added. The reaction mixture was stirred under nitrogen at ambient temperature for 12 h. Dichloromethane (300 mL) was then added and the reaction mixture was washed sequentially with 400 mL of 5% aqueous hydrochloride acid, 400 mL of saturated aqueous sodium bicarbonate solution, and 400 mL of brine, then dried over sodium sulfate, filtered, and concentrated in vacuo. Purification by flash chromatography (silica gel, 100% ethyl acetate to 10% methanol/ethyl acetate gradient elution) afforded the title compound. MS 367.2 (M+23).

INTERMEDIATE 3

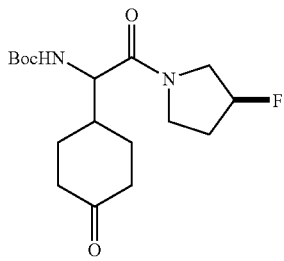

tert-Butyl [2-[(3S)-3-fluoropyrrolidin-1-yl]-2-oxo-1-(4-oxocyclohexyl)ethyl]carbamate To a solution of 2.0 g (5.9 mmol) of Intermediate 2 in 100 mL of dichloromethane was added 2.7 g (7.4 mmol) of the Dess-Martin periodinane reagent. The reaction mixture was stirred at ambient temperature for 3 h, then quenched with 50 mL of saturated aqueous sodium sulfite solution. This mixture was stirred for 5 min, then 50 mL of saturated aqueous sodium bicarbonate solution was added and the mixture stirred for an additional 15 min. The organic layer was then washed sequentially with 100 mL of saturated aqueous sodium sulfite solution, 100 mL of saturated aqueous sodium bicarbonate solution, and 100 mL of brine, dried over sodium sulfate, filtered and concentrated in vacuo. Purification by flash chromatography (silica gel, gradient elution, 80% ethyl acetate/hexane to 20% methanol/ethyl acetate) afforded the title compound. MS 243.1 (M+1−BOC).

INTERMEDIATE 4

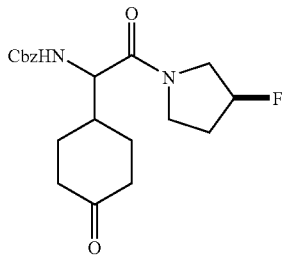

Benzyl [2-[(3S)-3-fluoropyrrolidin-1-yl]-2-oxo-1-(4-oxocyclohexyl)ethyl]carbamate To 1.6 g (4.7 mmol) of Intermediate 3 was added 20 mL of a 1:1 solution mixture of dichloromethane and trifluoroacetic acid. The solution was stirred for 30 min, then concentrated in vacuo. To the crude residue was added 60 mL of THF followed by 20 mL of aqueous saturated sodium bicarbonate solution and 0.67 mL (4.7 mmol) of benzyl chloroformate. The reaction mixture was stirred at ambient temperature for 90 min. Ethyl acetate (200 mL) was added, and the solution was washed sequentially with 200 mL of water, 200 mL of 5% aqueous hydrochloric acid, and 200 mL of brine, dried over sodium sulfate, filtered and concentrated in vacuo. Purification by flash chromatography (silica gel, gradient elution, 60% ethyl acetate/hexane to 100% ethyl acetate) afforded the title compound. MS 377.2 (M+1).

INTERMEDIATE 5

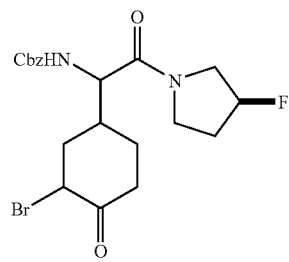

Benzyl [1-(3-bromo-4-oxocyclohexyl)-2-[(3S)-3-fluoropyrrolidin-1-yl]-2-oxoethyl]carbamate To 0.69 g (1.8 mmol) of Intermediate 4 in 25 mL of THF was added 1.32 g (3.5 mmol) of phenyltrimethylammonium perbromide at 0° C. The reaction mixture was allowed to stir and warm slowly to ambient temperature overnight. Saturated sodium bicarbonate solution (35 mL) was added and the reaction mixture was extracted with three 60 mL portions of ethyl acetate. The combined organics were washed with saturated aqueous sodium bicarbonate solution and brine, dried over sodium sulfate, filtered and concentrated in vacuo to the title compound. MS 456.2 (M+1).

INTERMEDIATE 6

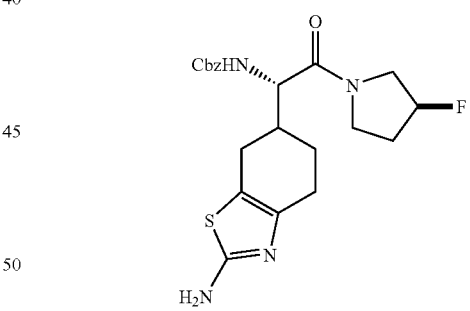

Benzyl {(1S)-1-(2-amino4,5,6,7-tetrahydro-1,3-benzothiazol-6-yl)-2-[(3S)-3-fluoropyrrolidin-1-yl]-2-oxoethyl}carbamate To 0.085 g (0.19 mmol) of Intermediate 5 was added 2 mL of absolute ethanol and 0.029 g (0.38 mmol) of thiourea, and the reaction mixture was stirred at 80° C. under nitrogen overnight. The reaction mixture was then cooled to room temperature and concentrated in vacuo. The crude product was purified directly on Gilson reverse phase preparative HPLC (YMC-Pack Pro C18, gradient elution, 10% acetonitrile/water to 90% acetonitrile/water in 9 min at 20 mL/min) to afford the aminothiazole. MS 433.3 (M+1).

INTERMEDIATE 7

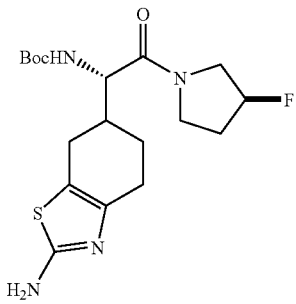

tert-Butyl [(1S)-1-(2-amino4,5,6,7-tetrahydro-1,3-benzothiazol-6-yl)-2-[(3S)-3-fluoropyrrolidin-1-yl]-2-oxoethyl]carbamate Intermediate 7 was formed from Intermediate 3 essentially following the procedures for Intermediates 5 and 6. The diastereomeric mixture was resolved using the ChiralCel OJ 4.6× 250 mm 10 micron column (70% ethanol/hexane). For the faster eluting diastereomer, MS 399.5 (M+1). For the slower eluting diastereomer, MS 399.5 (M+1).

EXAMPLE 1

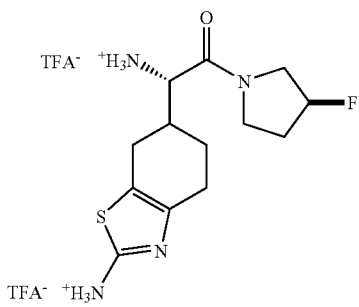

6-[(1S)-1-Amino-2-[(3S)-3-fluoropyrrolidin-1-yl]-2-oxoethyl]-4,5,6,7-tetrahydro-1,3-benzothiazol-2-amine, bis-trifluoroacetic acid salt Intermediate 6 was resolved using the ChiralCel OJ 4.6× 250 mm 10 micron column (70% ethanol/hexane) to afford each pure diastereomer of Intermediate 6.

To 18 mg (0.042 mmol) of the faster eluting diastereomer dissolved in 1 mL of acetonitrile was added 0.036 mL (0.25 mmol) of iodotrimethylsilane. The reaction mixture was stirred at ambient temperature for 30 min and then concentrated in vacuo. The crude product was purified directly on Gilson reverse phase preparative HPLC (YMC-Pack Pro C18, gradient elution, 10% acetonitrile/water to 90% acetonitrile/water in 9 min at 20 mL/min) to obtain one diastereomer of the title compound. MS 299.0 (M+1). The same procedure was used to afford the other diastereomer of the title compound from the slower eluting diastereomer of Intermediate 6. MS 299.0 (M+1).

EXAMPLE 2

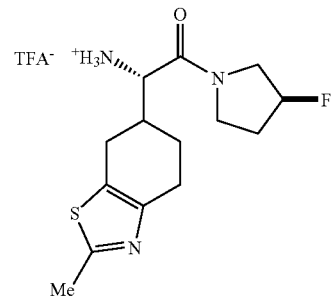

[(1S)-2-[(3S)-3-Fluoropyrrolidin-1-yl]-1-(2-methyl-4,5,6,7-tetrahydro-1,3-benzothiazol-6-yl)-2-oxoethyl]amine, trifluoroacetic acid salt To 0.17 g (0.38 mmol) of the α-bromoketone Intermediate 5 in 2 mL of DMF was added 42 mg (0.56 mmol) of thioacetamide. The reaction mixture was stirred at 80° C. under nitrogen for approximately 16 h. The reaction mixture was extracted with three 25-mL portions of ethyl acetate, and the organic phase was washed sequentially with two 50-mL portions of water and one 50-mL portion of brine, dried over sodium sulfate, filtered and concentrated in vacuo. The product was purified by flash chromatography (silica gel, gradient elution, 25% ethyl acetate/hexane to 75% ethyl acetate/hexane) to afford 45 mg of the diastereomeric mixture. The mixture was resolved by HPLC using the ChiralCel OJ 4.6× 250 mm 10 micron column with 50% ethanol/hexane. The pure diastereomers were deprotected using iodotrimethylsilane, essentially following the procedure described in Example 1. The products were purified by Gilson reverse phase preparative HPLC (YMC-Pack Pro C18, gradient elution, 10% acetonitrile/water to 90% acetonitrile/water in 9 min at 20 mL/min) to afford each diastereomer. Product from the faster eluting diastereomer, MS 298.1 (M+1). Product from the slower eluting diastereomer, MS 298.1 (M+1).

EXAMPLE 3

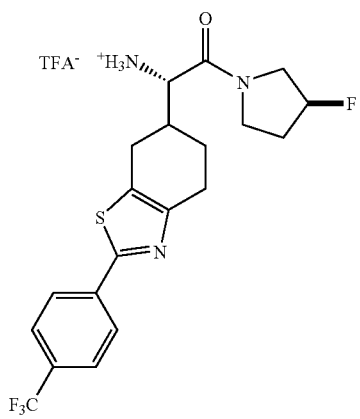

[(1S)-2-[(3S)-3-Fluoropyrrolidin-1-yl]-2-oxo-1-[2-[4-(trifluoromethyl)phenyl]-4,5,6,7-terahydro-1,3-benzothiazol-6-yl]ethyl]amine, trifluoroacetic acid salt To 0.070 g (0.15 mmol) of the α-bromoketone Intermediate 5 in 2 mL of DMF was added 47 mg (0.23 mmol) of 4-(trifluoromethyl)thiobenzamide. The reaction mixture was stirred at 100° C. under nitrogen for 16 h and then diluted with 20 mL of water. The reaction mixture was extracted with three 25-mL portions of ethyl acetate, and the combined organics were washed sequentially with two 50-mL portions of water and one 50-mL portion of brine, dried over sodium sulfate, filtered and concentrated in vacuo. The product was purified by flash chromatography (silica gel, gradient elution, 25% ethyl acetate/hexane to 75% ethyl acetate/hexane) to afford 35 mg of the diastereomeric mixture. The mixture was resolved by HPLC, using the ChiralCel AS 4.6×250 mm 10 micron column with 50% ethanol/hexane. The pure diastereomers were deprotected as in Example 1 using iodotrimethylsilane. The products were purified by Gilson reverse phase preparative HPLC (YMC-Pack Pro C18, gradient elution, 10% acetonitrile/water to 90% acetonitrile/water in 9 min at 20 mL/min) to afford each diastereomer of the title compound. For product from faster eluting diastereomer, MS 428.3 (M+1). For product from slower eluting diastereomer, MS 428.3 (M+1).

EXAMPLE 4

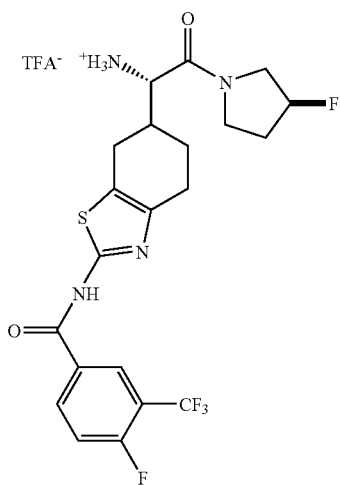

N-[6-[(1S)-1-Amino-2-[(3S)-3-fluoropyrrolidin-1-yl]-2-oxoethyl]-4,5,6,7-tetrahydro-1,3-benzothiazol-2-yl]-4-fluoro-3-(trifluoromethyl)benzamide, trifluoroacetic acid salt Intermediate 6 (40 mg, 0.092 mmol) was dissolved in 1 mL of dichloromethane, and 0.048 mL (0.28 mmol) of DIEA followed by 0.021 mL (0.14 mmol) of 4-fluoro-3-(trifluoromethyl)benzoyl chloride was added. The reaction mixture was stirred overnight at ambient temperature. The reaction mixture was filtered through 200 mg of PSA Bond Elut resin.

The resin was washed with 10 mL of 10% methanol/dichloromethane and the filtrate concentrated ini vacuo. The residue was purified by Gilson reverse phase preparative HPLC (YMC-Pack Pro C18, gradient elution, 10% acetonitrile/water to 90% acetonitrile/water in 9 min at 20 mL/min). The diastereomeric mixture was resolved by HPLC using the ChiralCel AS 4.6×250 mm 10 micron column with 50% ethanol/hexane. Protecting groups were removed following the procedure in Example 1 using iodotrimethylsilane and the products purified on Gilson reverse phase preparative HPLC (YMC-Pack Pro C18, gradient elution, 10% acetonitrile/water to 90% acetonitrile/water in 9 min at 20 mL/min) to obtain each diastereomer of the title compound. For the product from the faster eluting diastereomer, MS 489.2 (M+1). For the product from the slower eluting diastereomer, MS 489.2 (M+1).

EXAMPLE 5

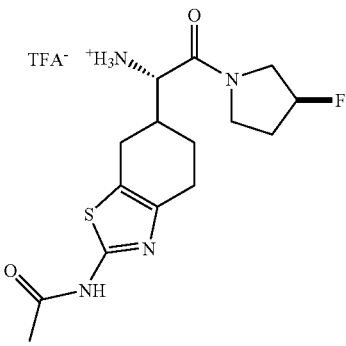

N-[6-[(1S)-1-Amino-2-[(3S)-3-fluoropyrrolidin-1-yl]-2-oxoethyl]-4,5,6,7-tetrahydro-1,3-benzothiazol-2-yl]acetamide, trifluoroacetic acid salt The faster eluting diastereomer of Intermediate 7 (19 mg, 0.075 mmol) was dissolved in 1 mL of dichloromethane with 0.040 mL (0.23 mmol) of DIEA and 0.011 mL (0.15 mmol) of acetyl chloride. The reaction mixture was stirred overnight at ambient temperature. The reaction mixture was then filtered through 200 mg of PSA Bond Elut resin. The resin was washed with 10 mL of 10% methanol/dichloromethane and the filtrate concentrated in vacuo and purified by Gilson reverse phase prep HPLC (YMC-Pack Pro C18, gradient elution, 10% acetonitrile/water to 90% acetonitrile/water in 9 min at 20 mL/min). The product was dissolved in 5 mL of a 1:1 mixture of dichloromethane and trifluoroacetic acid and stirred at ambient temperature for 30 min. The reaction mixture was concentrated in vacuo and the residue purified by Gilson reverse phase preparative HPLC (YMC-Pack Pro C18, gradient elution, 10% acetonitrile/water to 90% acetonitrile/water in 9 min at 20 mL/min) to obtain the title compound. MS 341.1 (M+1).

EXAMPLE 6

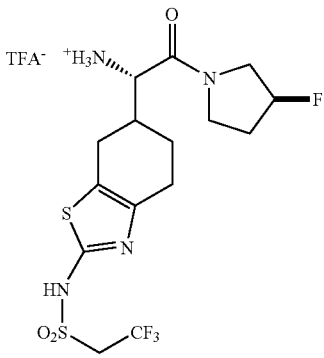

N-(6-{(1S)-1-Amino-2-[(3S)-3-fluoropyrrolidin-1-yl]-2-oxoethyl}-4,5,6,7-tetrahydro-1,3-benzothiazol-2-yl)-2,2,2-trifluoroethanesulfonamide, trifluoroacetic acid salt The faster eluting diastereomer of Intermediate 7 (60 mg, 0.15 mmol) was dissolved in 1 mL of dichloromethane, and 0.24 mL of pyridine (3 mmol) followed by 0.17 mL (1.5 mmol) of 2,2,2-trifluoroethanesulfonyl chloride was added. The reaction mixture was stirred overnight at ambient temperature. The reaction mixture was filtered through 200 mg of PSA Bond Elut resin. The resin was washed with 10 mL of 10% methanol/dichloromethane and the filtrate concentrated in vacuo. The residue was purified by Gilson reverse phase prep HPLC (YMC-Pack Pro C18, gradient elution, 10% acetonitrile/water to 90% acetonitrile/water in 9 min at 20 mL/min). The product was dissolved in 5 mL of a 1:1 mixture of dichloromethane and trifluoroacetic acid and the mixture stirred at ambient temperature for 30 min. The reaction mixture was then concentrated in vacuo. The residue was purified by Gilson reverse phase prep HPLC (YMC-Pack Pro C18, gradient elution, 10% acetonitrile/water to 90% acetonitrile/water in 9 min at 20 mL/min) to afford the title compound. MS 445.1 (M+1).

EXAMPLE 7

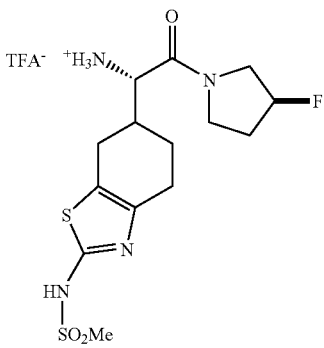

N-[6-[(1S)-1-Amino-2-[(3S)-3-fluoropyrrolidin-1-yl]-2-oxoethyl]-4,5,6,7-tetrahydro-1,3-benzothiazol-2-yl]methanesulfonamide, trifluoroacetic acid salt The title compound was prepared from the faster eluting diastereomer of Intermediate 7 and methanesulfonyl chloride, essentially following the procedure described in Example 6. MS 377.2 (M+1).

EXAMPLE OF A PHARMACEUTICAL FORMULATION

As a specific embodiment of an oral pharmaceutical composition, a 100 mg potency tablet is composed of 100 mg of any of the compounds of the present invention, 268 mg microcrystalline cellulose, 20 mg of croscarmellose sodium, and 4 mg of magnesium stearate. The active, microcrystalline cellulose, and croscarmellose are blended first. The mixture is then lubricated by magnesium stearate and pressed into tablets.

While the invention has been described and illustrated with reference to certain particular embodiments thereof, those skilled in the art will appreciate that various adaptations, changes, modifications, substitutions, deletions, or additions of procedures and protocols may be made without departing from the spirit and scope of the invention. For example, effective dosages other than the particular dosages as set forth herein above may be applicable as a consequence of variations in responsiveness of the mammal being treated for any of the indications with the compounds of the invention indicated above. The specific pharmacological responses observed may vary according to and depending upon the particular active compounds selected or whether there are present pharmaceutical carriers, as well as the type of formulation and mode of administration employed, and such expected variations or differences in the results are contemplated in accordance with the objects and practices of the present invention. It is intended, therefore, that the invention be defined by the scope of the claims which follow and that such claims be interpreted as broadly as is reasonable.

What is claimed is
1. A compound of structural formula I:

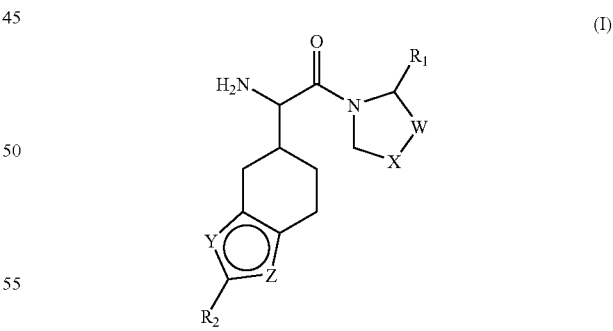

wherein:
each n is independently 0, 1, 2, or 3;
W is selected from the group consisting of $CH_2$, CHF, and $CF_2$;
X is selected from the group consisting of S, S(O), $S(O)_2$, $CH_2$, CHF, and $CF_2$;
Y and Z are each independently selected from the group consisting of O, S, N, and $NR^7$, with the proviso that at least one of Y and Z is N;

R¹ is hydrogen or cyano;
R² is selected from the group consisting of
  hydrogen,
  halogen,
  cyano,
  hydroxy,
  $C_{1-6}$ alkyl, wherein alkyl is unsubstituted or substituted with one to five halogens,
  $C_{1-6}$ alkoxy, wherein alkoxy is unsubstituted or substituted with one to five halogens,
  $(CH_2)_n$—COOH,
  $(CH_2)_n$—COOC$_{1-6}$ alkyl,
  $(CH_2)_n$—CONR³R⁴,
  $(CH_2)_n$—NR³R⁴,
  $(CH_2)_n$—NR⁶SO₂R⁵,
  $(CH_2)_n$—NR⁶CONR³R⁴,
  $(CH_2)_n$—NR⁶COR⁶,
  $(CH_2)_n$—NR⁶CO₂R⁵,
  $(CH_2)_n$-aryl, wherein aryl is unsubstituted or substituted with one to five substituents independently selected from halogen, hydroxy, CO₂H, $C_{1-6}$ alkyloxycarbonyl, $C_{1-6}$ alkyl, $C_{3-6}$ cycloalkyl, and $C_{1-6}$ alkoxy, wherein alkyl and alkoxy are unsubstituted or substituted with one to five halogens,
  wherein any methylene (CH₂) carbon atom in R² is independently unsubstituted or substituted with one to two groups independently selected from halogen, hydroxy, and
  $C_{1-4}$ alkyl unsubstituted or substituted with one to five halogens;
R³ and R⁴ are independently selected from the group consisting of
  hydrogen,
  $(CH_2)_n$-phenyl,
  $(CH_2)_n$—$C_{3-6}$ cycloalkyl, and
  $C_{1-6}$ alkyl,
  wherein alkyl is unsubstituted or substituted with one to five halogens and wherein phenyl and cycloalkyl are unsubstituted or substituted with one to five substituents independently selected from halogen, hydroxy, $C_{1-6}$ alkyl, and $C_{1-6}$ alkoxy, wherein alkyl and alkoxy are unsubstituted or substituted with one to five halogens; or
R³ and R⁴ together with the nitrogen atom to which they are attached form a heterocyclic ring selected from azetidine, pyrrolidine, piperidine, piperazine, and morpholine wherein said heterocyclic ring is unsubstituted or substituted with one to three substituents independently selected from halogen, hydroxy, $C_{1-6}$ alkyl, and
$C_{1-6}$ alkoxy, wherein alkyl and alkoxy are unsubstituted or substituted with one to five halogens;
each R⁵ is independently selected from the group consisting of $(CH_2)_n$-phenyl, $(CH_2)_n$—$C_{3-6}$ cycloalkyl, and $C_{1-6}$ alkyl, wherein alkyl is unsubstituted or substituted with one to five halogens and wherein phenyl and cycloalkyl are unsubstituted or substituted with one to five substituents independently selected from halogen, hydroxy, $C_{1-6}$ alkyl, and $C_{1-6}$ alkoxy, wherein alkyl and alkoxy are unsubstituted or substituted with one to five halogens, and wherein any methylene (CH₂) carbon atom in R⁵ is unsubstituted or substituted with one to two groups independently selected from halogen, hydroxy, and $C_{1-4}$ alkyl unsubstituted or substituted with one to five halogens;
each R⁶ is hydrogen or R⁵; and
R⁷ is selected from the group consisting of
  hydrogen,
  $(CH_2)_n$-phenyl,
  $(CH_2)_n$—$C_{3-6}$ cycloalkyl, and
  $C_{1-6}$ alkyl,
  wherein alkyl is unsubstituted or substituted with one to five halogens and wherein phenyl and cycloalkyl are unsubstituted or substituted with one to five substituents independently selected from halogen, hydroxy, $C_{1-6}$ alkyl, and $C_{1-6}$ alkoxy, wherein alkyl and alkoxy are unsubstituted or substituted with one to five halogens.

2. The compound of claim 1 wherein the carbon atom marked with an * has the stereochemical configuration as depicted in formula IIa:

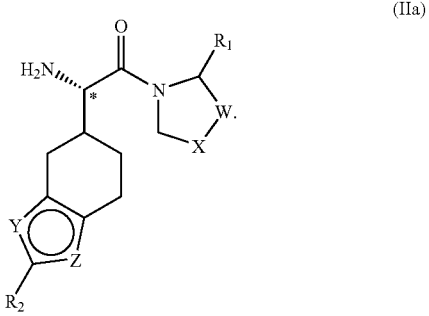

(IIa)

3. The compound of claim 1 of structural formula IIb:

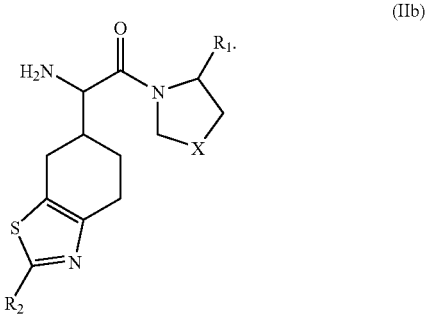

(IIb)

4. The compound of claim 3 wherein X is CH₂, CHF, or CF₂ and R¹ is hydrogen.

5. The compound of claim 3 wherein the carbon atom marked with an * has the stereochemical configured as depicted in formula IIc:

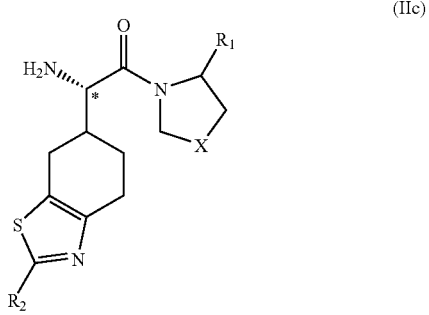

(IIc)

and wherein X is CH₂, CHF, or CF₂ and R¹ is hydrogen.

6. The compound of claim 1 of structural formula Id:

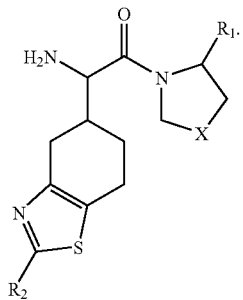
(IId)

7. The compound of claim 6 wherein X is $CH_2$, CHF, or $CF_2$ and $R^1$ is hydrogen.

8. The compound of claim 6 wherein the carbon atom marked with an * has the stereochemical configuration as depicted in formula IIe:

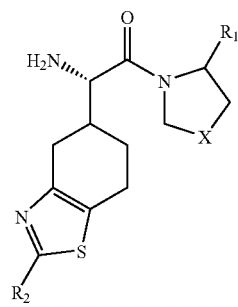
(IIe)

wherein X is $CH_2$, CHF, or $CF_2$ and $R^1$ is hydrogen.

9. The compound of claim 1 of structural formula IIf:

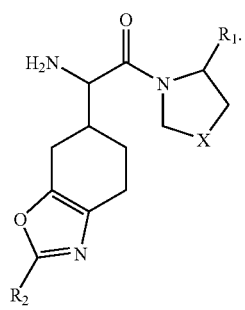
(IIf)

10. The compound of claim 9 wherein X is $CH_2$, CHF, or $CF_2$ and $R^1$ is hydrogen.

11. The compound of claim 9 wherein the carbon atom marked with an * has the stereochemical configuration as depicted in formula IIg:

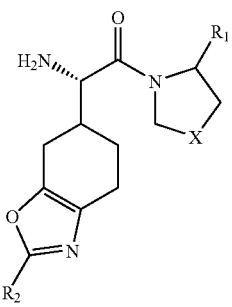
(IIg)

wherein X is $CH_2$, CHF, or $CF_2$ and $R^1$ is hydrogen.

12. The compound of claim 1 of structural formula IIh:

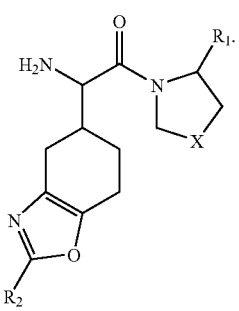
(IIh)

13. The compound of claim 12 wherein X is $CH_2$, CHF, or $CF_2$ and $R^1$ is hydrogen.

14. The compound of claim 12 wherein the carbon atom marked with an * has the stereochemical configuration as depicted in formula IIi:

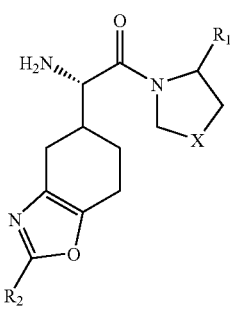
(IIi)

wherein X is $CH_2$, CHF, or $CF_2$ and $R^1$ is hydrogen.

15. The compound of claim 1 of structural formula IIj:

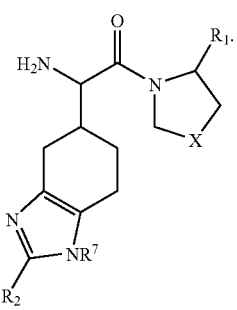
(IIj)

16. The compound of claim 15 wherein X is $CH_2$, CHF, or $CF_2$ and $R^1$ is hydrogen.

17. The compound of claim 15 wherein the carbon atom marked with an * has the stereochemical configuration as depicted in formula IIk:

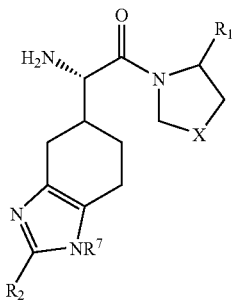

(IIk)

wherein X is $CH_2$, CHF, or $CF_2$ and $R^1$ is hydrogen.

18. The compound of claim 1 of structural formula III:

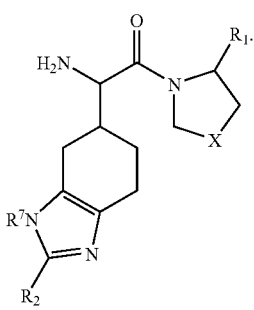

(III)

19. The compound of claim 18 wherein X is $CH_2$, CHF, or $CF_2$ and $R^1$ is hydrogen.

20. The compound of claim 18 wherein the carbon atom marked with an * has the stereochemical configuration as depicted in formula IIm:

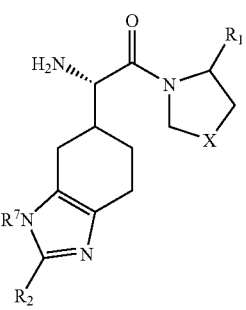

(IIm)

wherein X is $CH_2$, CHF, or $CF_2$ and $R^1$ is hydrogen.

21. A pharmaceutical composition which comprises a compound of claim 1 and a pharmaceutically acceptable carrier.

22. A method for treating non-insulin dependent (Type 2) diabetes in a mammal in need thereof which comprises the administration to the mammal of a therapeutically effective amount of a compound of claim 1.

* * * * *